(12) United States Patent
Weeber et al.

(10) Patent No.: US 9,454,018 B2
(45) Date of Patent: Sep. 27, 2016

(54) SYSTEM, OPHTHALMIC LENS, AND METHOD FOR EXTENDING DEPTH OF FOCUS

(75) Inventors: Hendrik Albert Weeber, Groningen (NL); Patricia Ann Piers, Groningen (NL); Pablo Artal, Murcia (ES); Silverstre Manzanera, Lorca (ES)

(73) Assignee: AMO Groningen B.V., Groningen (NL)

( * ) Notice: Subject to any disclaimer, the term of this patent is extended or adjusted under 35 U.S.C. 154(b) by 219 days.

(21) Appl. No.: 13/493,796

(22) Filed: Jun. 11, 2012

(65) Prior Publication Data

US 2013/0060330 A1     Mar. 7, 2013

Related U.S. Application Data

(62) Division of application No. 12/372,573, filed on Feb. 17, 2009, now abandoned.

(60) Provisional application No. 61/029,284, filed on Feb. 15, 2008.

(51) Int. Cl.
*A61F 2/16*     (2006.01)
*G02C 7/02*     (2006.01)

(52) U.S. Cl.
CPC ............... *G02C 7/02* (2013.01); *A61F 2/1613* (2013.01); *A61F 2/1637* (2013.01); *G02C 2202/20* (2013.01); *G02C 2202/22* (2013.01)

(58) Field of Classification Search
CPC .......................... A61F 2/1613; A61F 2/1637
See application file for complete search history.

(56) References Cited

U.S. PATENT DOCUMENTS

| | | |
|---|---|---|
| 2,077,092 A | 4/1937 | Broder |
| 3,305,294 A | 2/1967 | Alvarez |
| 3,367,734 A | 2/1968 | Bystricky et al. |
| 3,735,685 A | 5/1973 | Plummer |
| 4,010,496 A | 3/1977 | Neefe |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen |
| 4,249,272 A | 2/1981 | Poler |

(Continued)

FOREIGN PATENT DOCUMENTS

| | | |
|---|---|---|
| DE | 8107675 U1 | 7/1981 |
| EP | 226400 A2 | 6/1987 |

(Continued)

OTHER PUBLICATIONS

Alfonso J.F., et al., "Prospective Study of the Acri.LISA bifocal Intraocular Lens," Journal of Cataract Refractive Surgery, 2007, vol. 33 (11), pp. 1930-1935.

(Continued)

*Primary Examiner* — David H Willse
*Assistant Examiner* — Javier Blanco
(74) *Attorney, Agent, or Firm* — Abbott Medical Optics Inc.

(57) ABSTRACT

System, ophthalmic lens, and method for extending depth of focus includes an optic having a clear aperture disposed about a central axis. The optic includes a first surface and an opposing second surface. The first and second surfaces are configured to introduce an asymmetric aberration to the eye while maintaining the in-focus visual acuity.

4 Claims, 24 Drawing Sheets

(56) References Cited

U.S. PATENT DOCUMENTS

| | | |
|---|---|---|
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | LeMaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee et al. |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,225,858 A | 7/1993 | Portney |
| 5,229,797 A | 7/1993 | Futhey et al. |
| 5,258,025 A | 11/1993 | Fedorov et al. |
| 5,278,592 A | 1/1994 | Marie et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,652,638 A | 7/1997 | Roffman et al. |
| 5,691,800 A | 11/1997 | Iki et al. |
| 5,699,142 A | 12/1997 | Lee et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A * | 10/1999 | Werblin et al. ............... 623/6.34 |
| 6,015,435 A | 1/2000 | Valunin et al. |
| 6,051,024 A | 4/2000 | Cumming |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,261,321 B1 | 7/2001 | Kellan |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 * | 5/2006 | Lindacher et al. ...... 351/159.41 |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,794,497 B2 | 9/2010 | Brady et al. |
| 7,857,451 B2 | 12/2010 | Thibos et al. |
| 7,871,162 B2 | 1/2011 | Weeber |

(56) References Cited

U.S. PATENT DOCUMENTS

| | | |
|---|---|---|
| 8,382,281 B2 | 2/2013 | Weeber |
| 8,480,228 B2 | 7/2013 | Weeber |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0021824 A1 | 2/2004 | Ye et al. |
| 2004/0054358 A1 | 3/2004 | Cox |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 | 8/2004 | Piers et al. |
| 2004/0167622 A1 | 8/2004 | Sunalp et al. |
| 2004/0230299 A1 | 11/2004 | Simpson et al. |
| 2005/0096226 A1 | 5/2005 | Stock et al. |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0068453 A1 | 3/2006 | Altieri |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0176572 A1 | 8/2006 | Fiala |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1* | 12/2006 | Liang ............................ 351/246 |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0231809 A1 | 9/2008 | Haigis |
| 2008/0269642 A1 | 10/2008 | Deacon et al. |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0268158 A1 | 10/2009 | Weeber |
| 2009/0279048 A1 | 11/2009 | Hong et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0130888 A1 | 5/2010 | Deacon et al. |
| 2010/0161048 A1 | 6/2010 | Schaper, Jr. |
| 2010/0274234 A1* | 10/2010 | Liang ................................ 606/5 |
| 2012/0140166 A1 | 6/2012 | Zhao |

FOREIGN PATENT DOCUMENTS

| | | |
|---|---|---|
| EP | 227357 A2 | 7/1987 |
| EP | 0343067 A1 | 11/1989 |
| EP | 457553 A2 | 11/1991 |
| EP | 681198 A1 | 11/1995 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1310267 B1 | 1/2008 |
| EP | 1424049 B1 | 6/2009 |
| FR | 2745711 A1 | 9/1997 |
| WO | 8603961 A1 | 7/1986 |
| WO | WO9222264 A1 | 12/1992 |
| WO | WO9303409 A1 | 2/1993 |
| WO | 9507487 A1 | 3/1995 |
| WO | 9856315 A1 | 12/1998 |
| WO | WO0019906 A1 | 4/2000 |
| WO | 0111418 A1 | 2/2001 |
| WO | 0135868 A1 | 5/2001 |
| WO | 0154569 A1 | 8/2001 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | WO03009053 A1 | 1/2003 |
| WO | WO2004034129 A1 | 4/2004 |
| WO | WO2004090611 A2 | 10/2004 |
| WO | WO2004096014 A2 | 11/2004 |
| WO | WO2005019906 A1 | 3/2005 |
| WO | 2006032263 A2 | 3/2006 |
| WO | WO2006025726 A1 | 3/2006 |
| WO | WO2006047698 A1 | 5/2006 |
| WO | WO2006060477 A2 | 6/2006 |
| WO | WO2006060480 A2 | 6/2006 |
| WO | 2007067872 A2 | 6/2007 |
| WO | WO2007092948 A1 | 8/2007 |
| WO | WO2007133384 A2 | 11/2007 |
| WO | WO2008045847 A2 | 4/2008 |
| WO | 2008083283 A2 | 7/2008 |
| WO | 2009020963 A1 | 2/2009 |
| WO | 2009029515 A1 | 3/2009 |
| WO | WO2009076670 A1 | 6/2009 |
| WO | 2009137491 A1 | 11/2009 |
| WO | 2010009254 A1 | 1/2010 |
| WO | 2010009257 A1 | 1/2010 |

OTHER PUBLICATIONS

Canovas C., et al., "Hybrid Adaptive-Optics Visual Simulator," Optical Letters, 2010, vol. 35 (2), pp. 196-198.

Cohen, Allen L., "Practical design of a bifocal hologram contact lens or intraocular lens," Applied Optics, 1992, 31 (19), 3750-3754.

Co-pending U.S. Appl. No. 12/771,550, filed Apr. 30, 2010.

Diffractive Lenses for Extended Depth of Focus and Presbyopic Correction. Presentation from Wavefront Congress held on Feb. 15, 2008, Rochester, New York .

Doskolovich L.L., et al., "Special Diffractive Lenses," SPIE, 1992, vol. 1780, pp. 393-402.

International Search Report and Written Opinion for Application No. PCT/IB2011/001067, mailed on Sep. 13, 2011, 13 pages.

International Search Report for Application No. PCT/EP2008/061235, mailed on Mar. 5, 2009, 2 pages.

International Search Report for Application No. PCT/EP2009/051783, mailed on Apr. 28, 2009, 3 pages.

International Search Report for Application No. PCT/IB2009/005590, mailed on Sep. 30, 2009, 3 pages.

International Search Report for Application No. PCT/US08/073999, mailed on Dec. 3, 2008, 3 pages.

International Search Report for Application No. PCT/US09/042449, mailed on Nov. 5, 2009, 5 pages.

International Search Report for Application No. PCT/US2010/038167, mailed on Sep. 27, 2010, 2 pages.

Liou H.L., et al., "Anatomically Accurate, Finite Model Eye for Optical Modeling," Journal of Optical Society of America, 1997, vol. 14 (8), pp. 1684-1695.

(56) References Cited

OTHER PUBLICATIONS

Marsack J.D., et al., "Metrics of Optical Quality Derived From Wave Aberrations Predict Visual Performance," Journal of Vision, 2004, vol. 4 (4), pp. 322-328.
Monsoriu J.A., et al., "Devil's Lenses," Optics Express, 2007, vol. 15 (21), pp. 13858-13864.
Norrby S., et al., "Model Eyes for Evaluation of Intraocular Lenses," Applied Optics, 2007, vol. 46 (26), pp. 6595-6605.
Partial International Search Report for Application No. PCT/US2010/061081, mailed on Apr. 6, 2011, 2 pages.
Piers P.A., et al., "Eye Models for the Prediction of Contrast Vision in Patients with New Intraocular Lens Designs," Optics Letters, 2004, vol. 29 (7), pp. 733-735.
Piers P.A., et al, "Theoretical Comparison of Aberration-Correcting Customized and Aspheric Intraocular Lenses," Journal of Refractive Surgery, 2007, vol. 23 (4), pp. 374-384.
Siedlecki D., et al., "Radial Gradient index Intraocular Lens: a Theoretical Model," Journal of Modern Optics, 2008, vol. 55 (4-5), pp. 639-647.
Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.
U.S. Appl. No. 12/129,155, filed May 29, 2008.
U.S. Appl. No. 11/618,325, filed Dec. 29, 2006 (Brady et al).
U.S. Appl. No. 11/618,411, filed Dec. 29, 2006(Bradyetai).
U.S. Appl. No. 12/109,251, filed Apr. 24, 2008.
Van Meeteren A., "Calculations on the Optical Modulation Transfer Function of the Human Eye for White Light," Optica Acta, 1974, vol. 21 (5), pp. 395-412.
Vanden Berg T.J., "Analysis of Intraocular Straylight, Especially in Relation to Age," Optometry and Vision Science, 1995, vol. 72 (2), pp. 52-59.
Villegas E.A., et al., "Correlation between Optical and Psychophy, Sical Parameters as a Function of Defocus," Optometry and Vision Science, 2002, vol. 79 (1), pp. 60-67.
Co-pending U.S. Appl. No. 12/503,267, filed Jul. 15, 2009.
Alio J.L., et al., "Phakic Anterior Chamber Lenses for the Correction of Myopia: A 7—Year Cumulative Analysis of complications in 263 Cases," Ophthalmology, 1999, vol. 106 (3), pp. 458-466.
Apple D.J., et al., "Anterior Chamber Lenses Part 1: Complications and Pathology and a Review of Designs," Journal of Cataract Refractive Surgery, 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, 1989, vol. 36 (1), pp. 21-36.
Apple D.J., et al., Eds., "Intraocular Lenses: Evolution, Designs, Complications and Pathology," in: New Concepts in Intraocular Lens Implantation, Williams & Wilkins publisher, 1989, vol. 22 (36), pp. 205-221.
Baikoff G., et al., "Angle-fixated Anterior Chamber Phakic Intraocular Lens for Myopia 7 to -19 Diopters," Journal of Refractive Surgery, 1998, vol. 14 (3), pp. 282-292.
Cheng X., et al., "Predicting Subjective Judgment of Best Focus with Objective Image Quality Metrics," Journal of Vision, 2004, vol. 4 (4), pp. 310-321.
CILCO Advertisement Brochure, Oct. 1982, 3 pages.
De Almeida M.S., et al., "Different Schematic Eyes and their Accuracy to the in Vivo Eye: A Quantitative Comparison Study," Brazilian Journal of Physics, 2007, vol. 37 (2A), 10 pages.
Kim J.H., et al., "The Analysis of Predicted Capsular Bag Diameter using Modified Model of Capsule Measuring Ring in Asians," Clinical and Experimental Ophthalmology, 2008, vol. 36 (3), pp. 238-244.
Liou H.L., et al., "The Prediction of Spherical Aberration with Schematic Eyes," Ophthalmic and Physiological Optics, 1996, vol. 16 (4), pp. 348-354.
Marinho A., "Results are Encouraging for Phakic IOLs, but More Work is needed," Refractive Surgery, 2000, p. 12, 15.
Menapace R., "The Capsular Tension Rings," Journal of Cataract & Refractive Surgery, 2008, Chap. 3, pp. 27-44.
Navarro R., et al., "Accommodation-Dependent Model of the Human Eye with Aspherics," Journal of the Optical Society of America, 1985, vol. 2 (8), pp. 1273-1281.
Nio Y.K., et al., "Effect of Intraocular Lens Implantation on Visual Acuity, Contrast Sensitivity, and Depth of Focus," Journal of Cataract and Refractive Surgery, 2003, vol. 29 (11), pp. 2073-2081.
Olsen T., "Simple Method to Calculate the Surgically Induced Refractive Change," Journal of Cataract & Refractive Surgery, 1993, vol. 19 (2), pp. 319-320.
Praeger D.L., "Praeger Technique for the Insertion of the Copeland Radial IOL Posterior Chamber Placement," Copeland Lens, 1982, 7 pages.
Strenn K., et al., "Capsular bag Shrinkage after Implantation of an Open-Loop Silicone Lens and a Poly(methyl methacrylate) Capsule Tension Ring," Journal of Cataract and Refractive Surgery, 1997, vol. 23 (10), pp. 1543-1547.
Tehrani M., et al., "Capsule Measuring Ring to Predict Capsular Bag Diameter and Follow its Course after Foldable Intraocular Lens Implantation," Journal of Cataract Refractive Surgery, 2003, vol. 29 (11), pp. 2127-2134.
Vass C., et al., "Prediction of Pseudophakic Capsular bag Diameter based on Biometric Variables," Journal of Cataract and Refractive Surgery, 1999, vol. 25 (10), pp. 1376-1381.

* cited by examiner

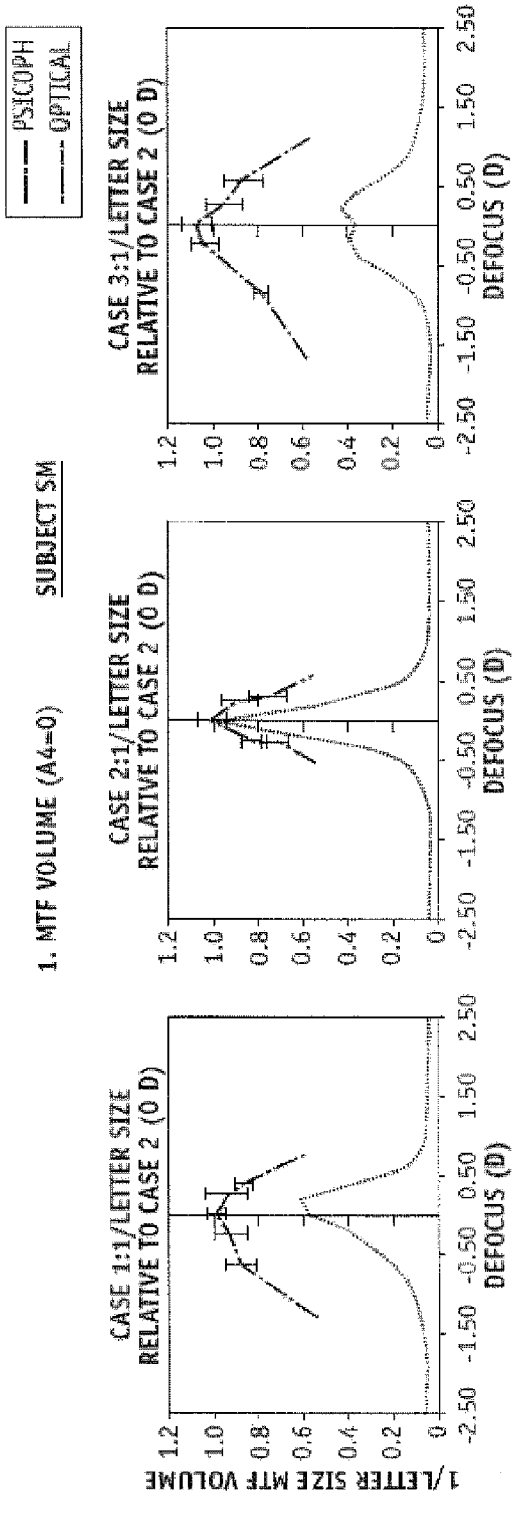
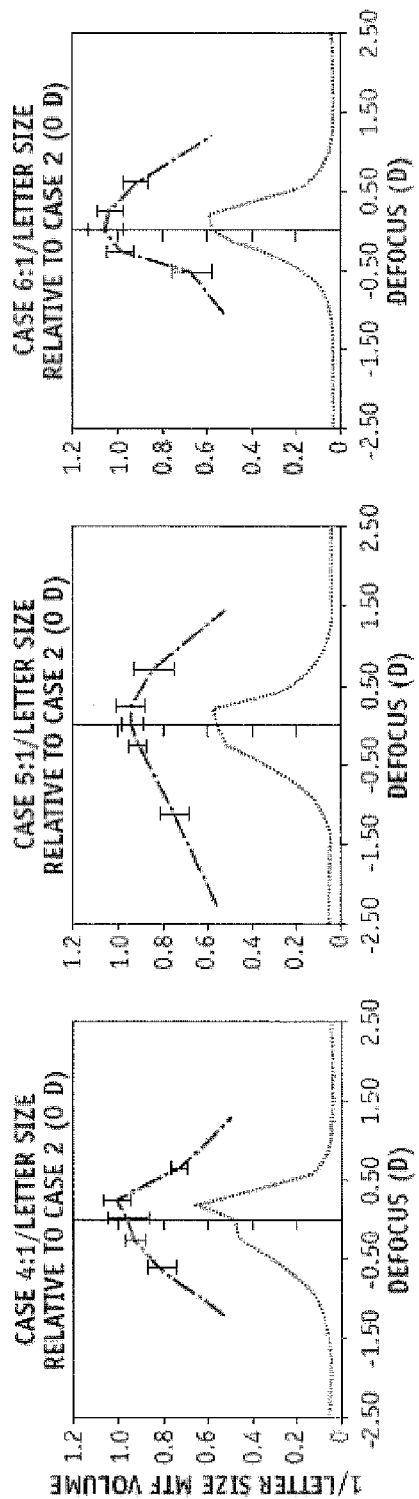
FIG. 10A  FIG. 10B  FIG. 10C
FIG. 10D  FIG. 10E  FIG. 10F

1. MTF VOLUME (A4=0)  SUBJECT EV
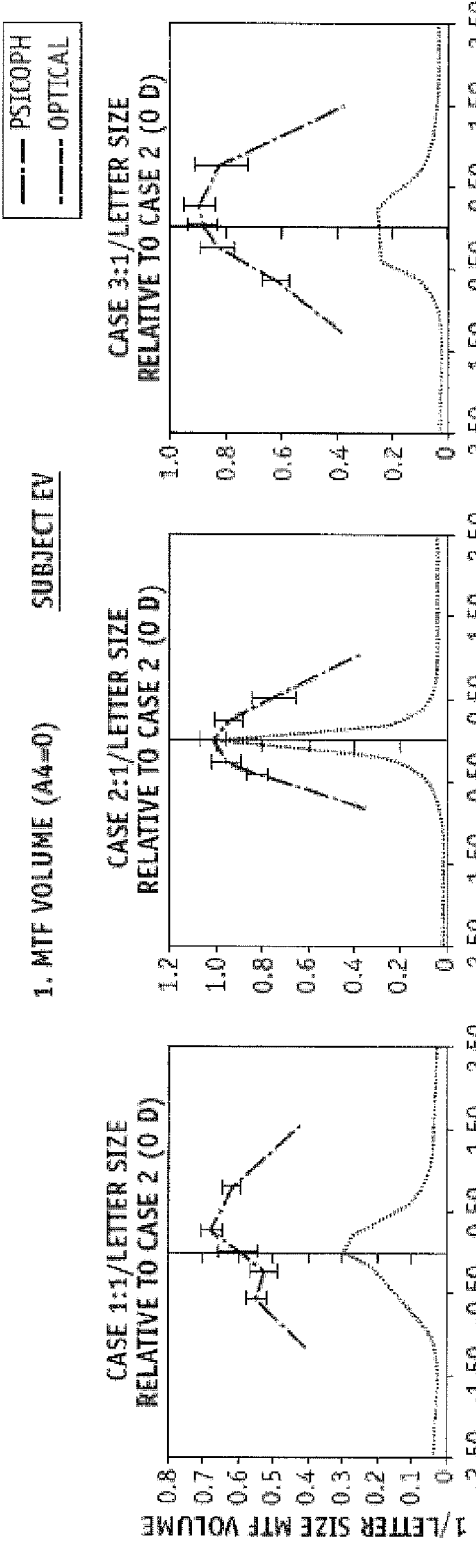
FIG. 11A
FIG. 11B
FIG. 11C
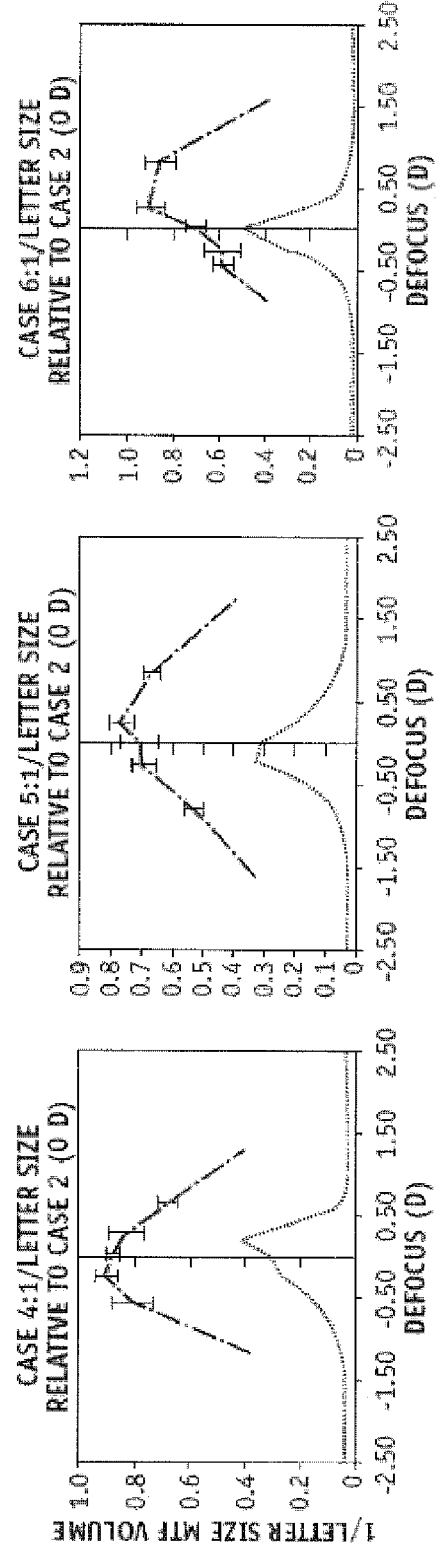
FIG. 11D
FIG. 11E
FIG. 11F

2. MTF AREA (A4=0)

6. MTF VOLUME AROUND A FREQUENCY RANGE (-10 cpd) (A4=0)

SYSTEM, OPHTHALMIC LENS, AND METHOD FOR EXTENDING DEPTH OF FOCUS

CROSS-REFERENCE TO RELATED APPLICATION

This application is a divisional application of U.S. patent application Ser. No. 12/372,573, entitled "SYSTEM, OPHTHALMIC LENS, AND METHOD FOR EXTENDING DEPTH OF FOCUS," filed Feb. 17, 2009, abandoned on Sep. 28, 2012, and claims priority to U.S. Provisional Application No. 61/029,284, filed Feb. 15, 2008, the entire contents of both of which are herein incorporated by reference in their entirety.

BACKGROUND OF THE INVENTION

1. Field of the Invention

The present invention relates generally to ophthalmic lenses and more specifically to intraocular lenses having an extended depth of focus.

2. Background

Intraocular lenses (IOLs) are commonly used to replace the natural lens of the eye under cataract conditions. Alternatively, the natural lens may be replaced to correct other visual conditions, for example, to provide accommodation or pseudo-accommodation in the event a subject develops presbyopia and has diminished focusing capability on both distant objects and near objects. "Accommodation" is the ability of the eye to change focus from near to far, far to near, and all distances in between. As presbyopia progresses, accommodation ability generally decreases. For example, with presbyopia, which usually begins at around age 40, the lens becomes less flexible. As the ciliary muscle contracts to move the lens forward, the lens typically resists due to presbyopia. Accommodating and/or multifocal intraocular lenses may be used to restore at least some degree of accommodative or pseudo-accommodative ability.

Accommodating intraocular lenses (AIOLs) are generally configured to focus on objects over a range of distances typically by moving axially and/or by changing shape in response to an ocular force produced by the ciliary muscle, zonules, and/or capsular bag of the eye. Current accommodating intraocular lenses are capable of providing about 0.5 diopter of objective accommodation. Multifocal intraocular lenses (MFIOLs) provide a pseudo-accommodation by simultaneously providing two or more foci, for example, one to provide distant vision and the other to provide near vision. This pseudo-accommodation may have some trade-off, such as dysphotopsia (e.g., halos or glare), reduced contrast sensitivity due to the continual presence of defocused light, reduced intermediate vision, pupil dependent performance, or the like. Over time, patients with multifocal intraocular lenses generally select the focus that provides the sharper image and ignore other blurred images.

Another approach to providing some degree of simulated accommodation is by extending the depth of focus of a traditional monofocal lens so that objects over a broader range of distances are simultaneously resolved. This approach also has some trade-off with reduced contrast sensitivity. Examples of this approach are discussed in U.S. Pat. Nos. 6,126,286, 6,923,539, and 7,061,692.

An intraocular lens is needed that extends the depth of focus of an eye while minimizing the occurrence of one or more factors reducing the optical performance of the eye, such as dysphotopsia, reduced contrast sensitivity, reduced intermediate vision, pupil dependent performance, or the like. More particularly, an intraocular lens is needed that extends the depth of focus of an eye without significantly reducing the in-focus visual acuity of the eye and while minimizing the occurrence of one or more factors reducing the optical performance of the eye, such as dysphotopsia, reduced contrast sensitivity, reduced intermediate vision, pupil dependent performance, or the like. Further, systems and methods for extending the depth of focus of the eye while minimizing the occurrence of one or more factors reducing the optical performance of the eye are needed.

SUMMARY OF THE INVENTION

The present invention is generally directed to ophthalmic devices, systems, and methods for extending the depth of focus of a subject's vision by introducing at least some higher order asymmetric aberration in the eye. The ophthalmic device may be an intraocular lens, a contact lens, a corneal inlay or onlay, a pair of spectacles, or the like. In some embodiments, the ophthalmic device may be a part of the structure of the natural eye, for example, the resulting corneal surface following a refractive procedure, such as a LASIK or PRK procedure. Embodiments of the present invention may find particular use in ophthalmic devices having a multifocal element (e.g., a diffractive or refractive lens producing two or more foci or images) or having accommodative capabilities.

In one aspect of the present invention, a lens for ophthalmic use, such as an intraocular lens, is provided. The lens includes an optic having a clear aperture disposed about a central axis. The optic includes a first surface and an opposing second surface. The first and second surfaces are together configured to introduce at least some asymmetric aberration in the eye to increase the depth of focus while maintaining the in-focus visual acuity of the eye. Maintaining in-focus visual acuity is referred to herein as having essentially the same letter acuity or reading acuity and/or having an identical functional acuity, which is regarded as normal for a particular age group, and which does not limit the functional vision. Maintaining in-focus visual acuity specifically excludes super-acuity, that is, acuity that significantly exceeds the acuity associated with normal 20/20 vision. In one embodiment, the ophthalmic lens introduces some degree of coma, or other higher order asymmetric aberration, in the eye while maintaining in-focus visual acuity of the eye.

In another embodiment, a lens system for an eye is provided, and the lens system includes a first lens having a first optical axis and a second lens adjacent the first lens. The second lens has a second optical axis being non-aligned with the first optical axis. The first lens and second lens are together configured to introduce at least some asymmetric aberration to the eye to extend the depth of focus while maintaining the in-focus visual acuity of the eye.

In another embodiment, a method is provided for modifying a depth of focus of an eye. The method includes measuring a wavefront aberration of the eye, determining an in-focus visual acuity of the eye, and determining an asymmetric aberration to be induced in the wavefront aberration of the eye. The depth of focus is extended by the asymmetric aberration when induced in the wavefront aberration and while maintaining the in-focus visual acuity.

In other embodiments, the present invention may be used in concert with a multifocal intraocular lens to extend all of the focal points thereof, with an accommodating intraocular lens to extend the functional range of vision available to the patient, with other extended depth of focus techniques, with targeted correction of other higher-order aberrations, with chromatic aberration correction, and the like.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following figures, with like numerals indicating like parts:

FIG. 10A-F illustrate comparisons of inverse letter size versus defocus for various aberration correction types of the first subject to Modulation Transfer Function volume versus defocus for the respective aberration correction types of the first subject;

FIG. 11A-F illustrate comparisons of inverse letter size versus defocus for various aberration correction types of the second subject to Modulation Transfer Function volume versus defocus for the respective aberration correction types of the second subject;

DETAILED DESCRIPTION

Figure 1:
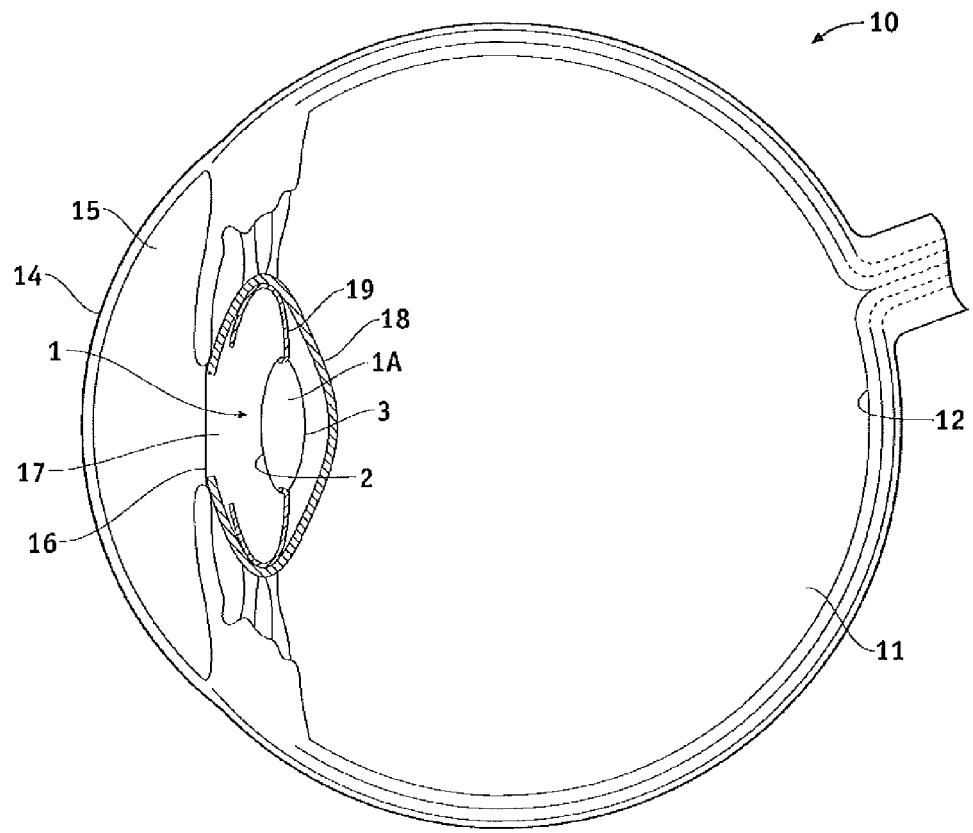
FIG. 1 is a schematic drawing of a human eye after implantation with an intraocular lens.

An ophthalmic lens, an ophthalmic system, and a method of modifying optical characteristics of an eye are provided in accordance with the present invention. In general, at least some asymmetric aberration is introduced in the eye to increase the depth of focus of the eye while maintaining in-focus visual acuity. Maintaining in-focus visual acuity is referred to herein as having essentially the same letter acuity or reading acuity or having an identical functional acuity, which is regarded as normal for a particular age group, and which does not limit the functional vision. Maintaining in-focus visual acuity specifically excludes super-acuity, that is, acuity that significantly exceeds the acuity associated with normal 20/20 vision.

In one embodiment, the ophthalmic lens introduces a higher order asymmetric aberration (e.g., some degree of coma or the like) in the eye while maintaining the in-focus visual acuity of the eye. Due to the near-spherical or substantially spherical geometry of the anterior surface of the cornea, two types of aberrations, spherical aberration and coma, may occur. The term "coma" is referred to herein as an optical aberration in which the image of a point source is generally a comet-shaped figure. Spherical aberration and coma are similar to one another by inadequately imaging or focusing rays at the same point. Coma differs from spherical aberration, however, in that a point object is imaged not as a circle but as a comet-shaped figure. Nevertheless, both cases are characterized by a loss of definition at the focal spot. By inducing an asymmetric aberration (e.g., coma or other higher order asymmetric aberration) to the wavefront aberration of a pseudophakic eye, the depth of focus may be increased.

In one embodiment, an ophthalmic lens with pre-determined bending factors (e.g., to produce asymmetric aberrations) introduces asymmetric aberration in the eye while maintaining in-focus visual acuity. For example, the ophthalmic lens may be formed with an asymmetric curvature on the anterior side of the corresponding optic, the posterior side of the corresponding optic, or a combination of the anterior and posterior side of the optic. In another embodiment, an ophthalmic lens may be lathe-cut (e.g., the surface of the lens may be lathed) to be rotationally asymmetric. In another embodiment, an ophthalmic lens may be molded to be rotationally asymmetric. For example, U.S. Pat. No. 5,620,720, the entire disclosure of which is incorporated herein, discloses a cast molding technique for forming intraocular lenses.

In another embodiment, the lens may be mechanically configured to be tilted or de-centered in the eye (e.g., by a controlled and pre-determined degree). For example, U.S. Pat. Nos. 5,567,365 and 5,571,177 and U.S. patent application Ser. No. 12/239,462 filed Sep. 26, 2008, to Deacon et al, the entire disclosures of which are incorporated herein, disclose various methods for modifying the orientation of an implanted intraocular lens.

In another embodiment, an Alvarez lens can be used and positioned to introduce a pre-determined degree of asymmetric aberration. For example, U.S. Pat. No. 3,305,294 discloses an Alvarez lens with lens elements that are movable relative to each other transversely to the optical axis of the lens and PCT Pub. No. WO/2006/025726 discloses an Alvarez-type intraocular lens, both of which are incorporated in entirety herein. In another embodiment, a dual lens system (e.g., axially positioned with respect to one another) that is de-centered with respect to one another may be used.

Other higher order asymmetrical aberrations may be used to extend or increase the depth of focus including, but not necessarily limited to, astigmatism, high-order astigmatism, vertical coma, lateral coma, trefoil, and the like, and combinations thereof may also be used. Examples of ophthalmic lenses include, but are not necessarily limited to, intraocular lenses, external lenses, contact lenses, intrastromal lens implants, implantable shaped corneal tissue, and the like.

Because each individual vision typically has a unique wavefront characteristic, the ophthalmic lens may similarly have a variety of configurations to introduce the asymmetric aberration while maintaining in-focus visual acuity. Detailed information about the wavefront characteristics associated with the eye (e.g., optical aberrations) may be acquired. Examples of such detailed information include, but are not necessarily limited to, the extent of a desired refractive correction, the location in the eye associated with the correction (e.g., where the correction can be made most effectively), and the like. Wavefront analysis techniques, made possible by devices such as a Hartmann-Shack type sensor, can be used to generate maps of refractive power. Other wavefront analysis techniques and sensors may also be used. The maps of refractive power, or similar refractive power information provided by other means, such as corneal topographs or the like, can then be used to identify and locate the optical aberrations that require correction.

The ophthalmic lens may also have multifocal characteristics. With a multifocal lens embodiment, the introduced asymmetric aberration preferably extends the depth of focus associated with all of the focal points of the multifocal lens. In other embodiments, the introduced asymmetric aberration can extend the depth of focus in either the near or the far focus position. In an accommodating lens embodiment, the lens with asymmetric aberration extends the functional range of vision available to the patient. Furthermore, the introduction of a pre-determined degree of asymmetric aberration (e.g., while maintaining in-focus visual acuity) can be combined with other extended depth of focus concepts, such as binary phase masks, lenses that utilize hyperfocality, zonal aspheric lenses, low-add multifocal lenses, and the like, with targeted correction of other higher-order aberrations, such as spherical aberration and/or astigmatism (e.g., using a toric lens), and/or with chromatic aberration correction (e.g., using a diffractive monofocal lens).

Referring to the drawings, a human eye 10 is shown in FIG. 1 after an intraocular lens 1 has been inserted. Light enters (e.g., from the left of FIG. 1) and passes through a cornea 14, an anterior chamber 15, an iris 16, and enters a capsular bag 17. Prior to insertion, the natural lens (not shown) occupies essentially the entire interior of the capsular bag 17. After insertion, the capsular bag 17 may house the intraocular lens 1, in addition to a fluid that occupies the remaining volume and equalizes the pressure in the eye 10. The intraocular lens 1 is preferably constructed to introduce an asymmetric aberration in the eye 10 without significantly reducing the in-focus visual acuity thereof. After passing through the intraocular lens 1, light exits a posterior wall 18 of the capsular bag 17, passes through a posterior chamber 11, and strikes the retina 12, which detects the light and converts it to a signal transmitted through the optic nerve to the brain.

The intraocular lens 1 has an optic 1a with a refractive index greater than the surrounding fluid. The optic 1a has an anterior surface 2 facing away from the retina 12 and a posterior surface 3 facing toward the retina 12. In this embodiment, the anterior surface 2 and posterior surface 3 are shaped to induce a predetermined amount of coma in the eye 10. In one embodiment, the anterior surface 2 is rotationally asymmetric with respect to the posterior surface 3. The optic 1a is held in place by a haptic 19, which couples the optic 1a to the capsular bag 17 after insertion. In the illustrated embodiment, the optic 1a is suspended within the capsular bag 17, for example, to allow accommodative movement of the optic 1a of the intraocular lens 1 along the optical axis, such as may be found with accommodative intraocular lenses. Alternatively, the intraocular lens 1 may be disposed adjacent to, and even biased against, the posterior wall 18, for example, to reduce cellular growth on the optic 1a. The optic 1a may be either a monofocal intraocular lens or a multifocal intraocular lens.

A well-corrected eye typically forms an image at the retina 12. If the lens 1 has too much or too little power, the image shifts axially along the optical axis away from the retina 12, toward or away from the lens. The power required to focus on a close or near object is generally greater than the power required to focus on a distant or far object. The difference in optical power between the farthest and nearest object that may be brought into focus by a particular lens or lens system is typically referred to as an "add power" (e.g., in the case of a multifocal intraocular lens) or a "range of accommodation" or "accommodative range" (e.g., in the case of an accommodating intraocular lens that responds to ciliary muscle contraction to move axially and/or deform so as to change the optical power of the optic). A normal range of add power or accommodation is generally about 4 Diopters at the plane of the optic 1a, although this number may be as low as 3 or fewer Diopters or as high as 6 or more Diopters based on the geometry of the eye.

Figure 2:
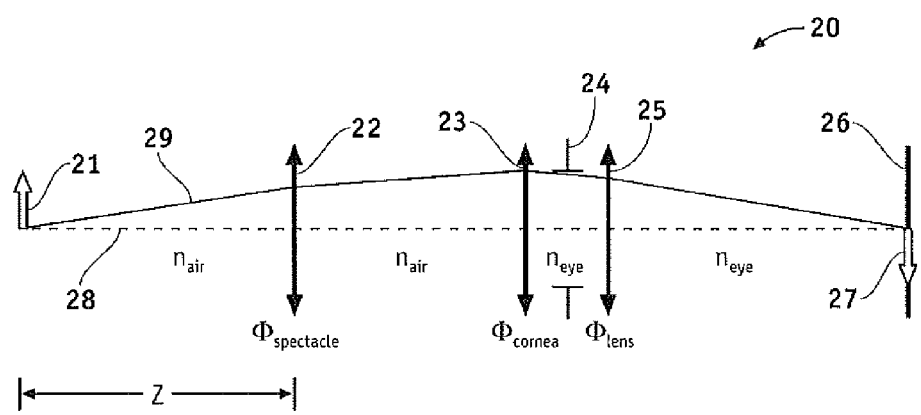
FIG. 2 is a schematic drawing of a thin lens model that approximates the human eye of FIG. 1.

In many cases, the optical system of the eye may be well approximated by a thin lens model, shown schematically in FIG. 2. Such a thin lens system 20 may be used to predict the location of an image for a given object distance, Z. In addition, the thin lens system 20 may also be used to predict the power required of a lens to bring objects at the object distance, Z, into focus on the retina. This may be used to predict or determine in-focus visual acuity for a particular optical system or eye.

A marginal light ray 29 originates at the base of an object 21, where the ray 29 crosses an optical axis 28. The ray 29 passes through an optional spectacle 22 having a power, $\phi$spectacle, and enters the eye. The eye itself is represented by a cornea 23 with a power, $\phi$cornea, an aperture stop (or pupil) 24, an intraocular lens 25 with a power, $\phi$lens, and a retina 26. An image 27 is formed of the object 21 at the location where the marginal ray 29 intersects the optical axis 28. If the object 21 is "in focus," then the image 27 is formed at the retina 26. If the object is "out of focus," then the image is translated axially away from the retina 26, being either too close to the lens or too far from the lens. The space between the object 21 and the cornea 23 is assumed to be filled with air, having a refractive index of $n_{air}$ (e.g., typically 1). The space between the cornea 23 and the retina 26 is assumed to be filled with a fluid having a refractive index of $n_{eye}$.

One exemplary figure of merit for tracking the performance of visual systems is known as a Modulation Transfer Function (MTF). The MTF generally indicates the ability of an optical system to reproduce (e.g., transfer) various levels of detail (e.g., spatial frequencies) from the object to the image. MTF is particularly desirable as a figure of merit because it may be both predicted by simulation and approximately measured through the visual response of real patients.

The MTF is related to the apparent contrast of alternating bright and dark bars of an image. If the MTF is 1, then the bright areas generally appear completely bright, and the dark areas generally appear completely dark. If the MTF is 0, both areas appear as gray, with generally little to no distinction between bright and dark areas. Typical MTF values lie between 0 and 1 with some light bleeding into the dark areas and some darkness bleeding into the light areas.

The MTF has a dependence on spatial frequency, which is inversely related to the width of the alternating bright and dark bars in the image. Note that MTF is particularly suited for human vision testing, in that the spatial frequency may be controlled during a test by controlling the size of a letter "E," where the widths of the prongs in the "E" have a prescribed size. MTF is measured along two orthogonal axes (e.g., an x-axis and a y-axis or a horizontal axis and a vertical axis).

Spatial frequency is typically reported in units of line pairs per mm at the retina. At low spatial frequencies (e.g., represented with wider bars), the MTF is generally higher than at high spatial frequencies (e.g., represented with narrower bars). For frequencies greater than a predetermined cutoff spatial frequency, the MTF is 0. This is a property governed by the physics of diffraction. MTF may be calculated in a straightforward numerical manner, either by a ray-tracing program such as Oslo or Zemax, by another existing simulation tool, or by self-written code, all of which provide generally equivalent results with varying degrees of sophistication.

Figure 3:
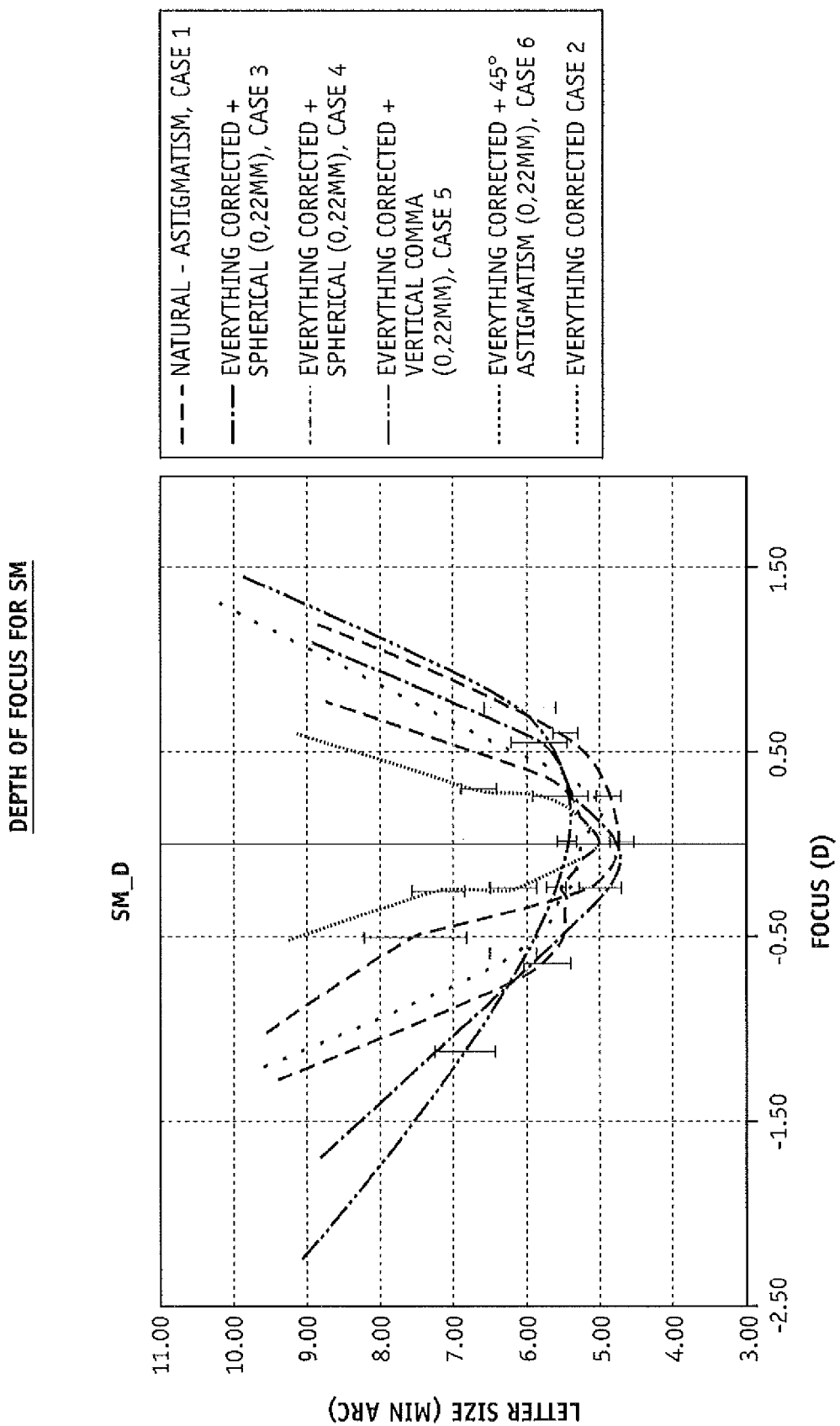
FIG. 3 is a plot of defocus versus minimum readable letter size, for a variety of aberration corrections, for a first subject.
Figure 4:
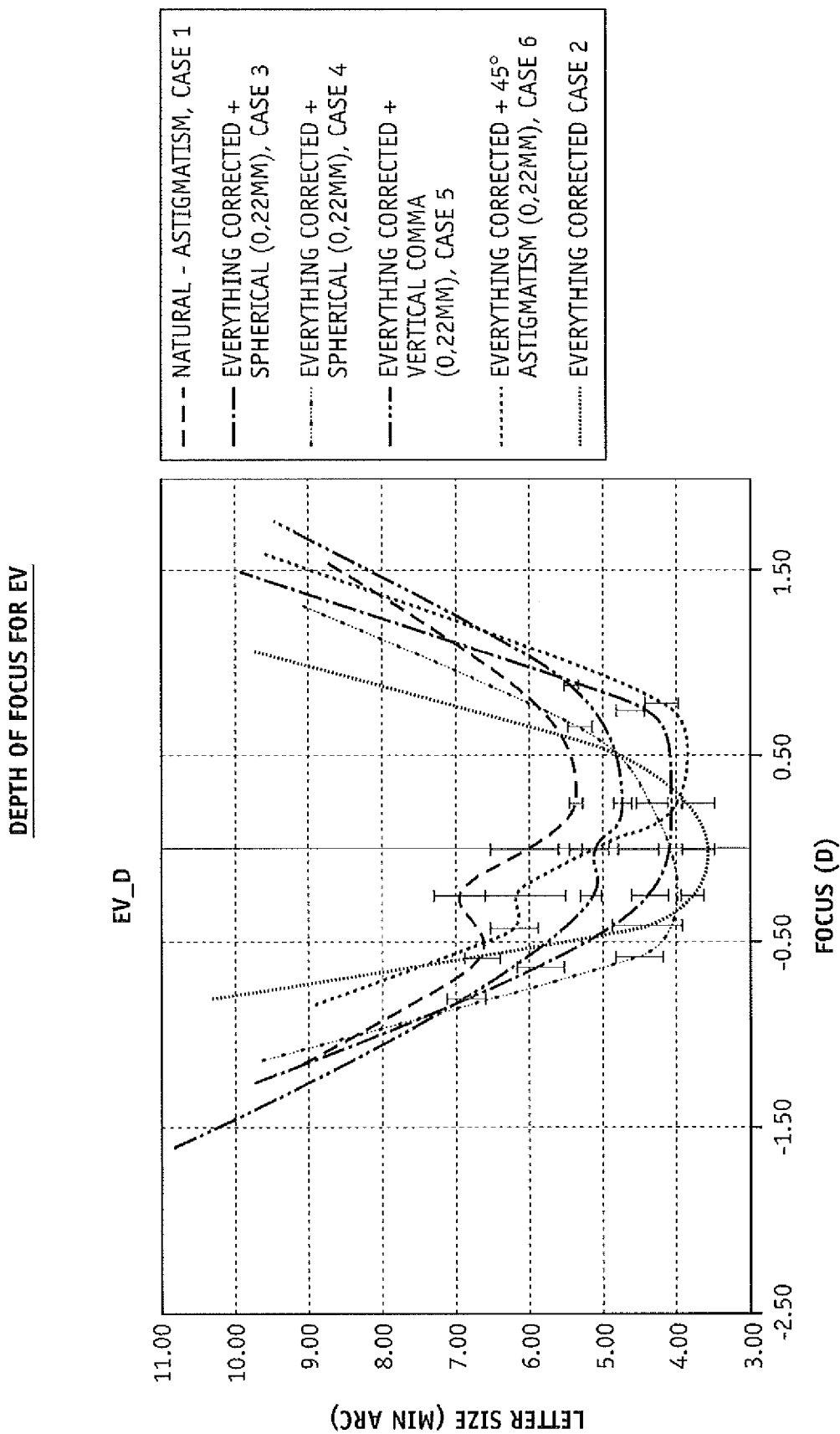
FIG. 4 is a plot of defocus versus minimum readable letter size, for a variety of aberration corrections, for a second subject.
Figure 5:
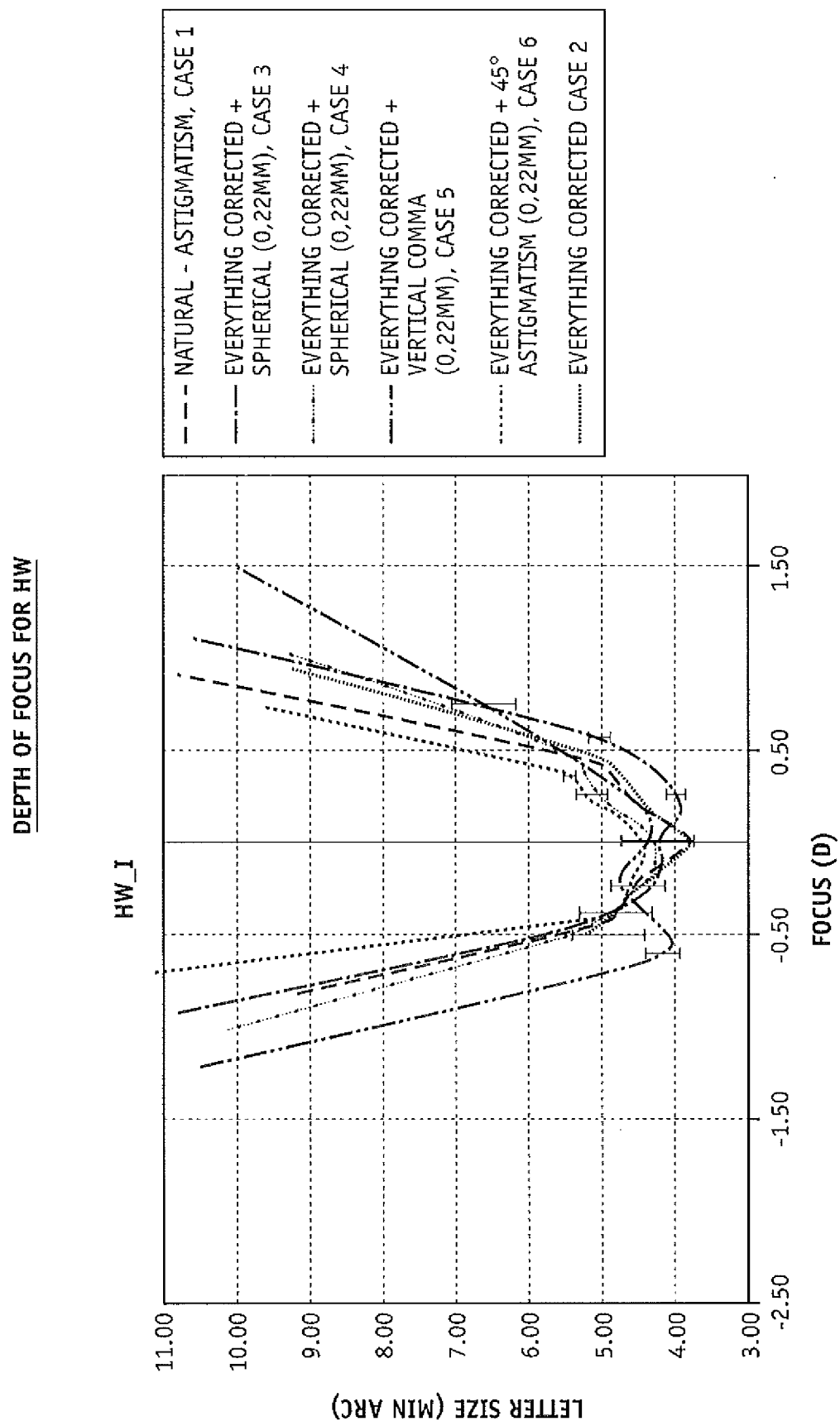
FIG. 5 is a plot of defocus versus minimum readable letter size, for a variety of aberration corrections, for a third subject.

FIG. 3 is a plot of minimum readable letter size versus defocus, for a variety of aberration corrections, for a first subject (SM). FIG. 4 is a plot of defocus versus minimum readable letter size, for a variety of aberration corrections, for a second subject (EV). FIG. 5 is a plot of defocus versus minimum readable letter size, for a variety of aberration corrections, for a third subject (HW). Six cases were used for comparison: case 1 is based on the naturally occurring higher-order aberrations of the subject with only lower-order astigmatism and defocus corrected; case 2 is based on a correction of all aberrations (e.g., no wavefront aberrations); case 3 is based on a correction of all aberrations except for a positive spherical aberration (e.g., 0.22 µm); case 4 is based on a correction of all aberrations except for a negative spherical aberration (e.g., −0.22 µm)); case 5 is based on a correction of all aberrations except for a coma aberration ((e.g., 0.22 µm)); and, case 6 is based on a correction of all aberrations except for an astigmatism aberration (e.g., 0.22 µm). As best shown in FIGS. 3-5, the introduction of coma (e.g., case 5) provided the greatest depth of focus for all three subjects.

Figure 6:
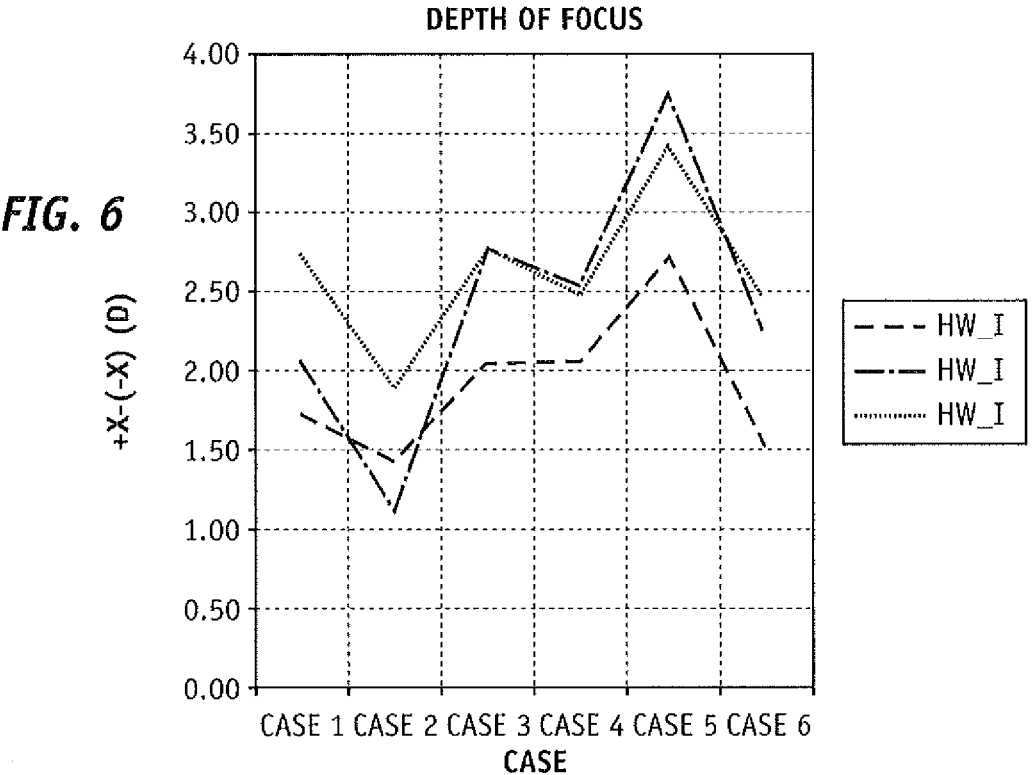
FIG. 6 is a plot of depth of focus versus the variety of aberration corrections shown in FIGS. 3-5, for each of the subjects.
Figure 7:
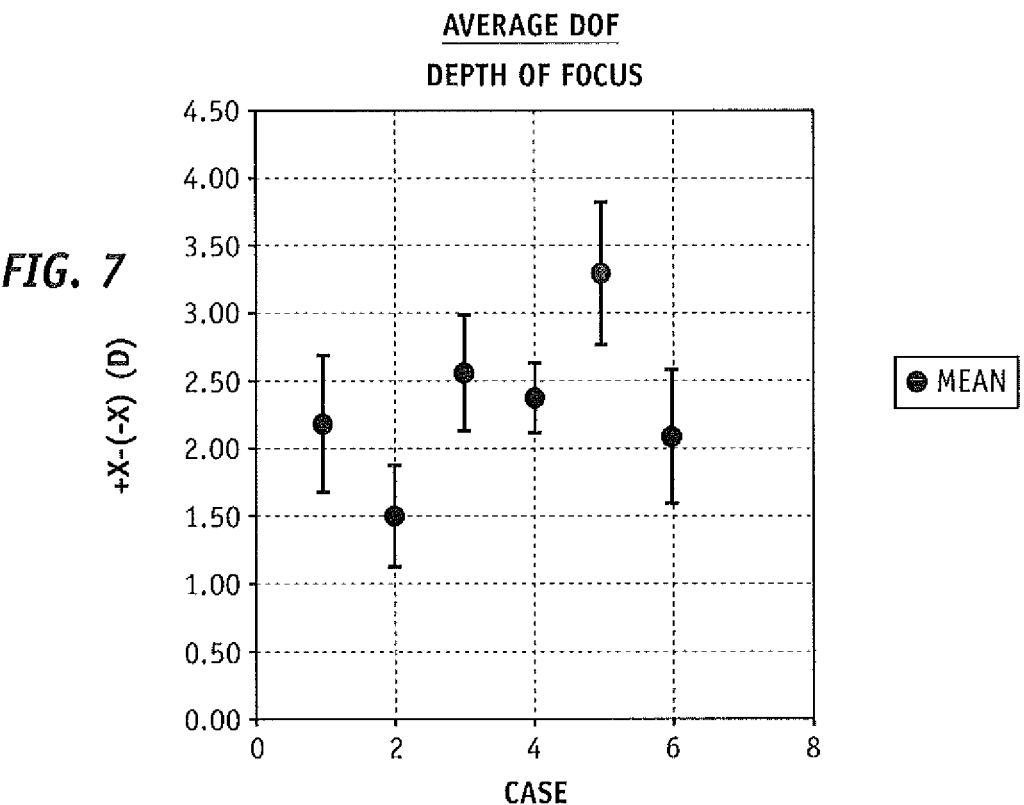
FIG. 7 is a graph of the depth of focus versus the variety of aberration corrections shown in FIGS. 3-5 illustrating the average focus depth for each of the variety of aberration corrections.
Figure 8:
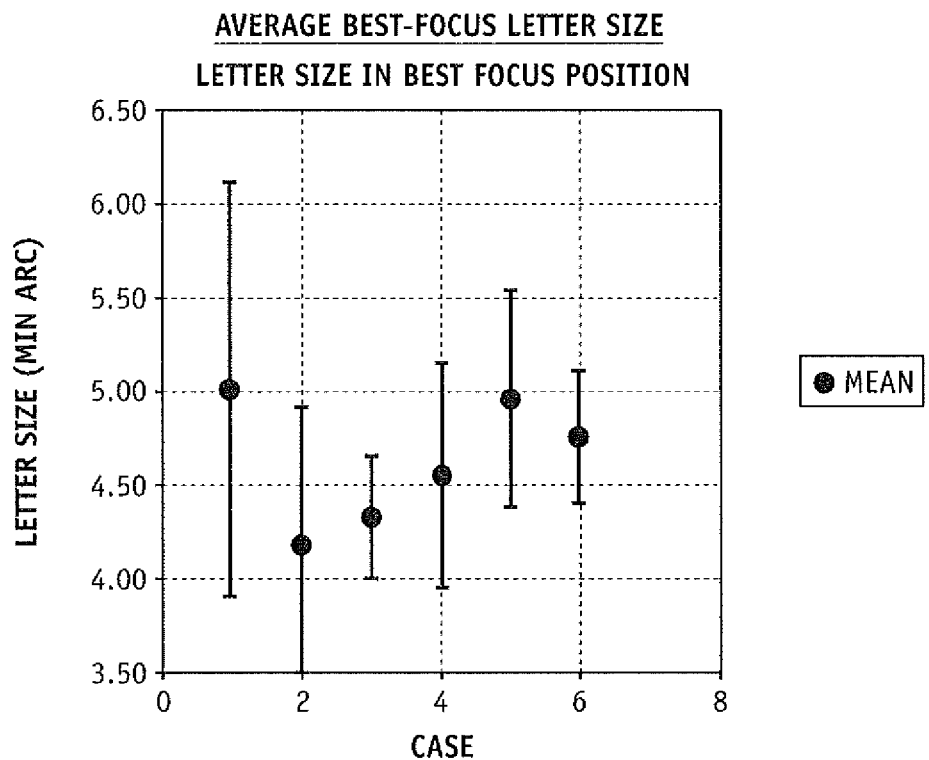
FIG. 8 is a graph of the minimum readable letter size versus the variety of aberration corrections shown in FIGS. 3-5 illustrating the minimum readable letter size for each of the variety of aberration corrections.

FIG. 6 is a plot of depth of focus versus the variety of aberration corrections shown in FIGS. 3-5, for each of the subjects. FIG. 7 is a graph of the depth of focus versus the variety of aberration corrections shown in FIGS. 3-5 illustrating the average focus depth for each of the variety of aberration corrections. FIG. 8 is a graph of the minimum readable letter size (e.g., in the best-focus position) versus the variety of aberration corrections shown in FIGS. 3-5 illustrating the minimum letter size for each of the variety of aberration corrections.

FIGS. 3-5 illustrate examples of induced aberrations that increase the depth of focus, while maintaining the in-focus acuity. In-focus acuity is explicitly shown in FIG. 8. For example, the cases 1 and 5 in FIG. 8 show the same in-focus acuity (letter size), while the depth of focus of these cases differ (such as shown in FIG. 7). Similarly, cases 5 and 6 in FIG. 8 show the same in-focus acuity (letter size), while the depth of focus of these cases differ (FIG. 7). As a third example, cases 2 and 3 in FIG. 8 show the same in-focus acuity (e.g., based on letter size), while the depth of focus of these cases differ (as shown in FIG. 7). This demonstrates that by adding aberrations and/or changing the aberrations in the eye, the depth of focus of the eye can be increased, without changing the in-focus acuity.

Figure 9:
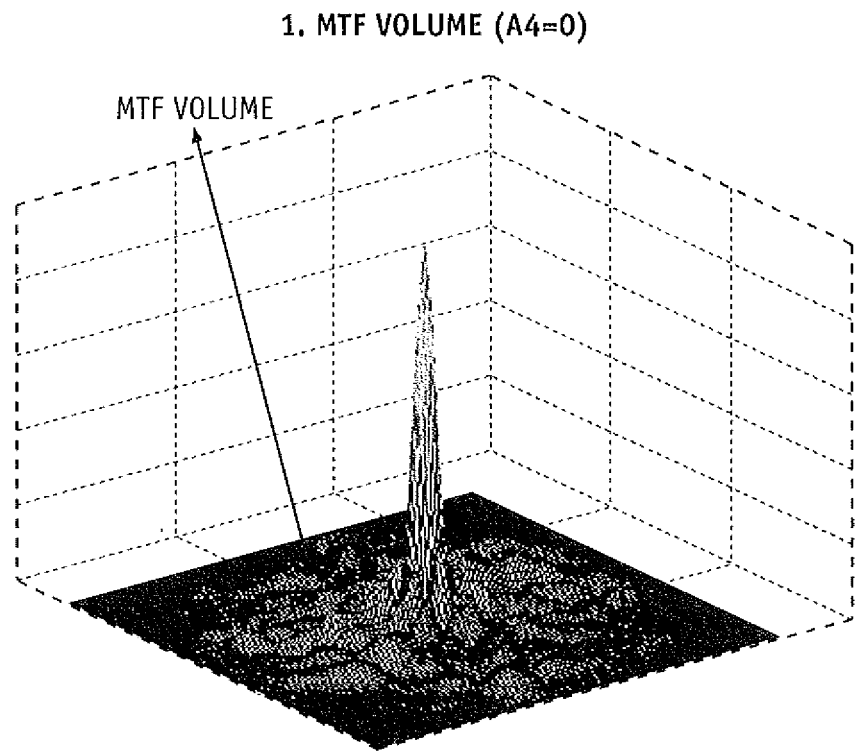
FIG. 9 is a Modulation Transfer Function (MTF) illustrating an MTF volume in one embodiment.

FIG. 9 is a Modulation Transfer Function (MTF) illustrating an MTF volume in one embodiment. FIG. 10 illustrates comparisons of inverse letter size versus defocus for various aberration correction types of the first subject to Modulation Transfer Function volume versus defocus for the respective aberration correction types of the first subject. For example, inverse letter size versus defocus for the first aberration correction type of the first subject is compared to Modulation Transfer Function volume versus defocus for the first aberration correction type of the first subject, inverse letter size versus defocus for the second aberration correction type of the first subject is compared to Modulation Transfer Function volume versus defocus for the second aberration correction type of the first subject, inverse letter size versus defocus for the third aberration correction type of the first subject is compared to Modulation Transfer Function volume versus defocus for the third aberration correction type of the first subject, inverse letter size versus defocus for the fourth aberration correction type of the first subject is compared to Modulation Transfer Function volume versus defocus for the fourth aberration correction type of the first subject, inverse letter size versus defocus for the fifth aberration correction type of the first subject is compared to Modulation Transfer Function volume versus defocus for the fifth aberration correction type of the first subject, and inverse letter size versus defocus for the sixth aberration correction type of the first subject is compared to Modulation Transfer Function volume versus defocus for the sixth aberration correction type of the first subject. The peak of the MTF curves is at zero defocus. In each of the comparisons, a pschophysical measurement (e.g., "psicoph") is compared with a theoretical calculation (e.g., "optical").

FIG. 11 illustrates comparisons of inverse letter size versus defocus for various aberration correction types of the first subject to Modulation Transfer Function area versus defocus for the respective aberration correction types of the first subject. For example, inverse letter size versus defocus for the first aberration correction type of the second subject is compared to Modulation Transfer Function volume versus defocus for the first aberration correction type of the second subject, inverse letter size versus defocus for the second aberration correction type of the second subject is compared to Modulation Transfer Function volume versus defocus for the second aberration correction type of the second subject, inverse letter size versus defocus for the third aberration correction type of the second subject is compared to Modulation Transfer Function volume versus defocus for the third aberration correction type of the second subject, inverse letter size versus defocus for the fourth aberration correction type of the second subject is compared to Modulation Transfer Function volume versus defocus for the fourth aberration correction type of the second subject, inverse letter size versus defocus for the fifth aberration correction type of the second subject is compared to Modulation Transfer Function volume versus defocus for the fifth aberration correction type of the second subject, and inverse letter size versus defocus for the sixth aberration correction type of the second subject is compared to Modulation Transfer Function volume versus defocus for the sixth aberration correction type of the second subject.

Figure 12:
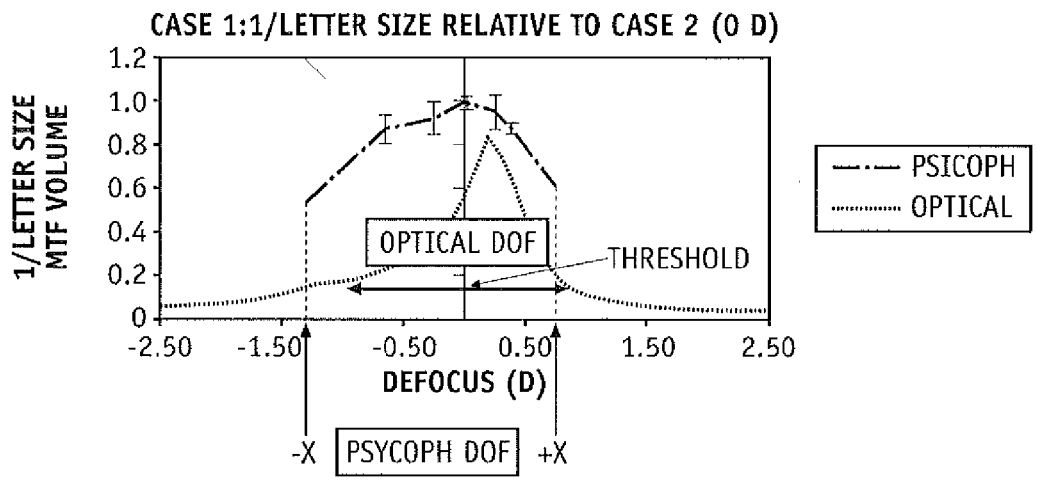
FIG. 12 illustrates comparisons is a plot of inverse letter size versus defocus illustrating depth of focus determination at a threshold in one example.

A depth of focus for a lens may be defined based on any number of criteria, such as a threshold of any of the MTF curves, a particular increase in spot size or wavefront error, a particular decrease in Strehl Ratio, or any other suitable criterion. FIG. 12 is a plot of inverse letter size versus defocus illustrating a depth of focus determination at a threshold, in one example. There are many possible definitions of depth of focus that many be used, as well as many other figures of merit that may be used for the definitions. For instance, any or all of the following optical metrics may be used: MTF at a particular spatial frequency, MTF volume (integrated over a particular range of spatial frequencies, either in one dimension or in two dimensions), Strehl ratio, encircled energy, RMS spot size, peak-to-valley spot size, RMS wavefront error, peak-to-valley wavefront error, and edge transition width. Given the many possible figures of merit, there are several ways to evaluate them to define a depth of focus.

One way is to define an absolute threshold, where the crossings of the figure of merit with the threshold define the depth of focus. For instance, the depth of focus may be defined as the region over which the MTF or MTF volume exceeds a threshold of 0.1. Alternatively, any suitable MTF absolute threshold may be used, such as 0.15, 0.2, 0.25, 0.3 and so forth. Alternatively, the depth of focus may be defined as the region over which the RMS spot size is less than a particular threshold value.

Figure 13:
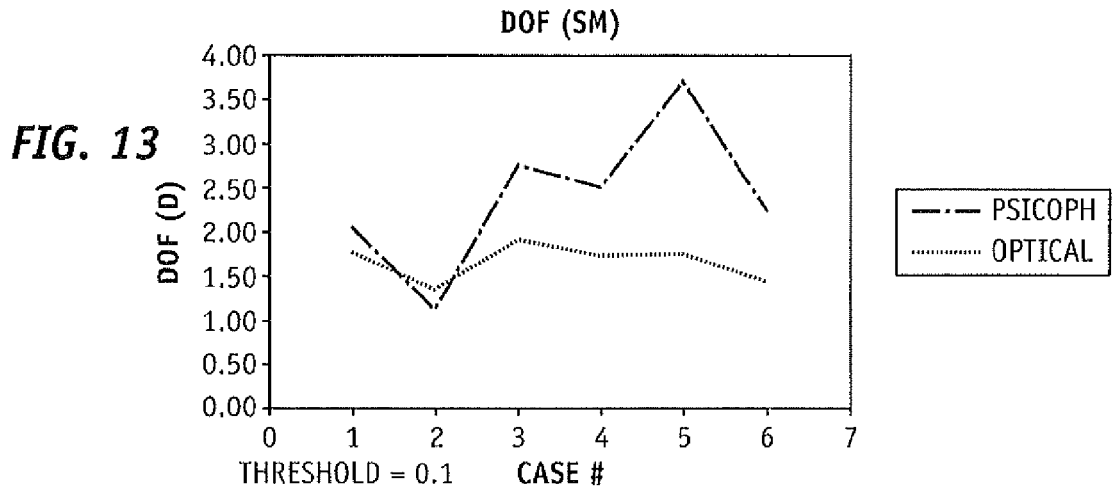
FIG. 13 is a plot of depth of focus versus the aberration correction types determined from the pschophysical measurement and determined from theoretical calculation of MTF volume shown in FIG. 10 of the first subject.
Figure 14:
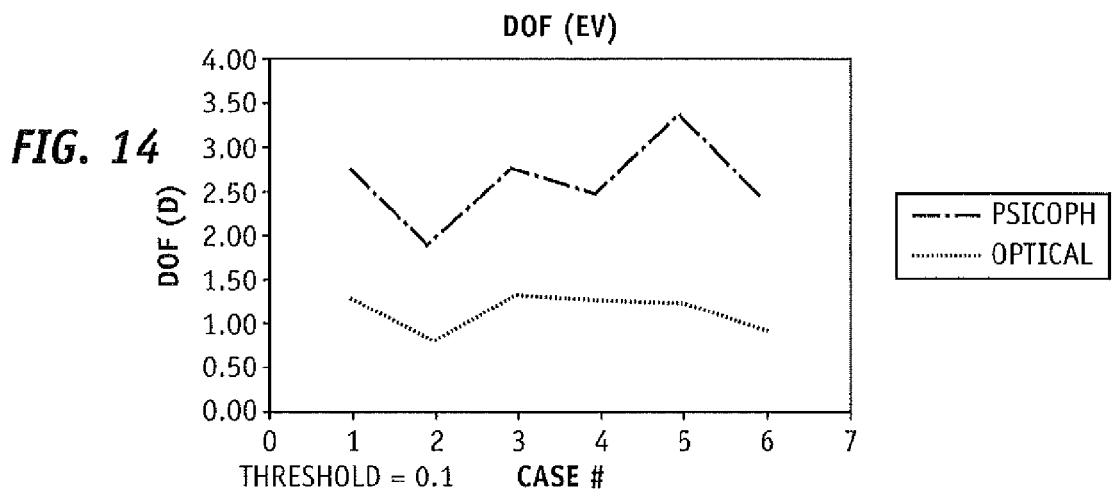
FIG. 14 is a plot of depth of focus versus the aberration correction types determined from the pschophysical measurement and determined from theoretical calculation of MTF volume shown in FIG. 11 of the second subject.

FIG. 13 is a plot of depth of focus versus the aberration correction types determined from the pschophysical measurement and determined from theoretical calculation of MTF volume shown in FIG. 10 of the first subject. FIG. 14 is a plot of depth of focus versus the aberration correction types determined from the pschophysical measurement and determined from theoretical calculation of MTF volume shown in FIG. 11 of the second subject.

Figure 15:
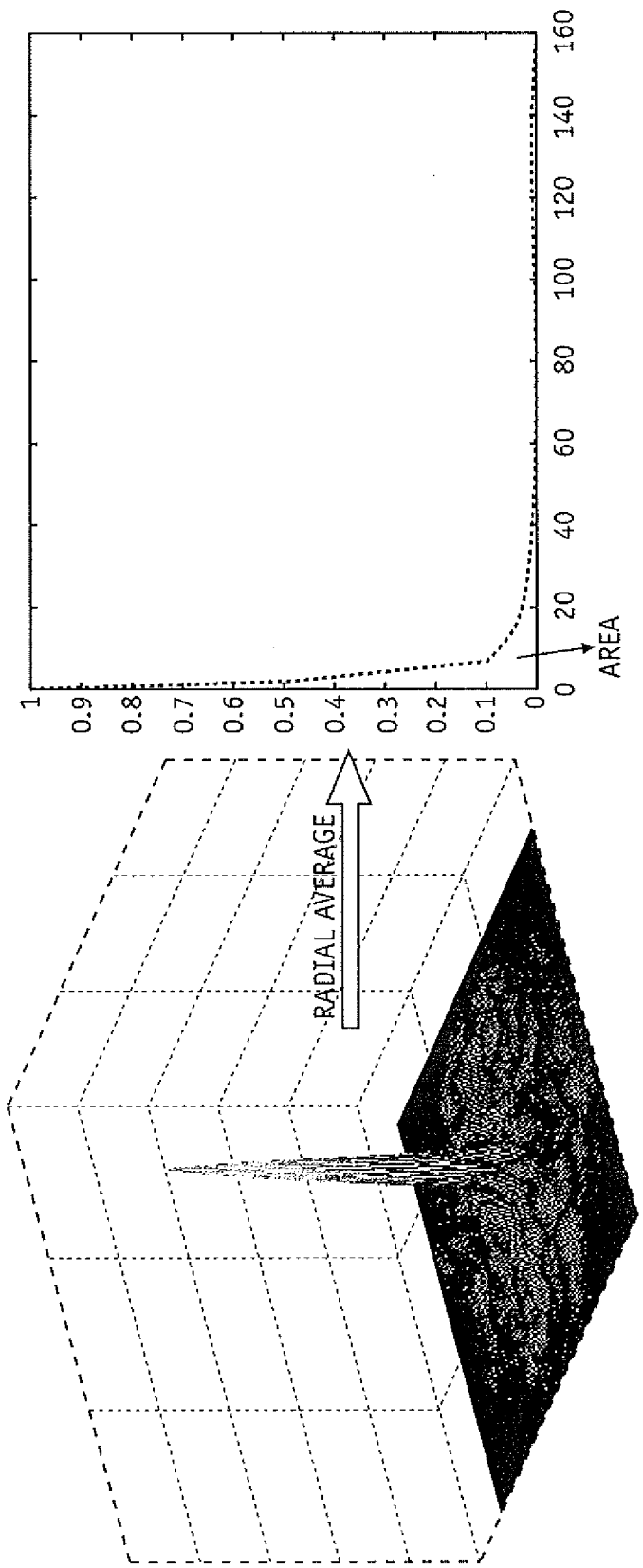
FIG. 15 is a Modulation Transfer Function illustrating an MTF area in one embodiment.

FIG. 15 is a Modulation Transfer Function illustrating an MTF area in one embodiment. The radial average (e.g., the averaged curvature at the center of the MTF curve) is used to determine the MTF area.

Figure 16:
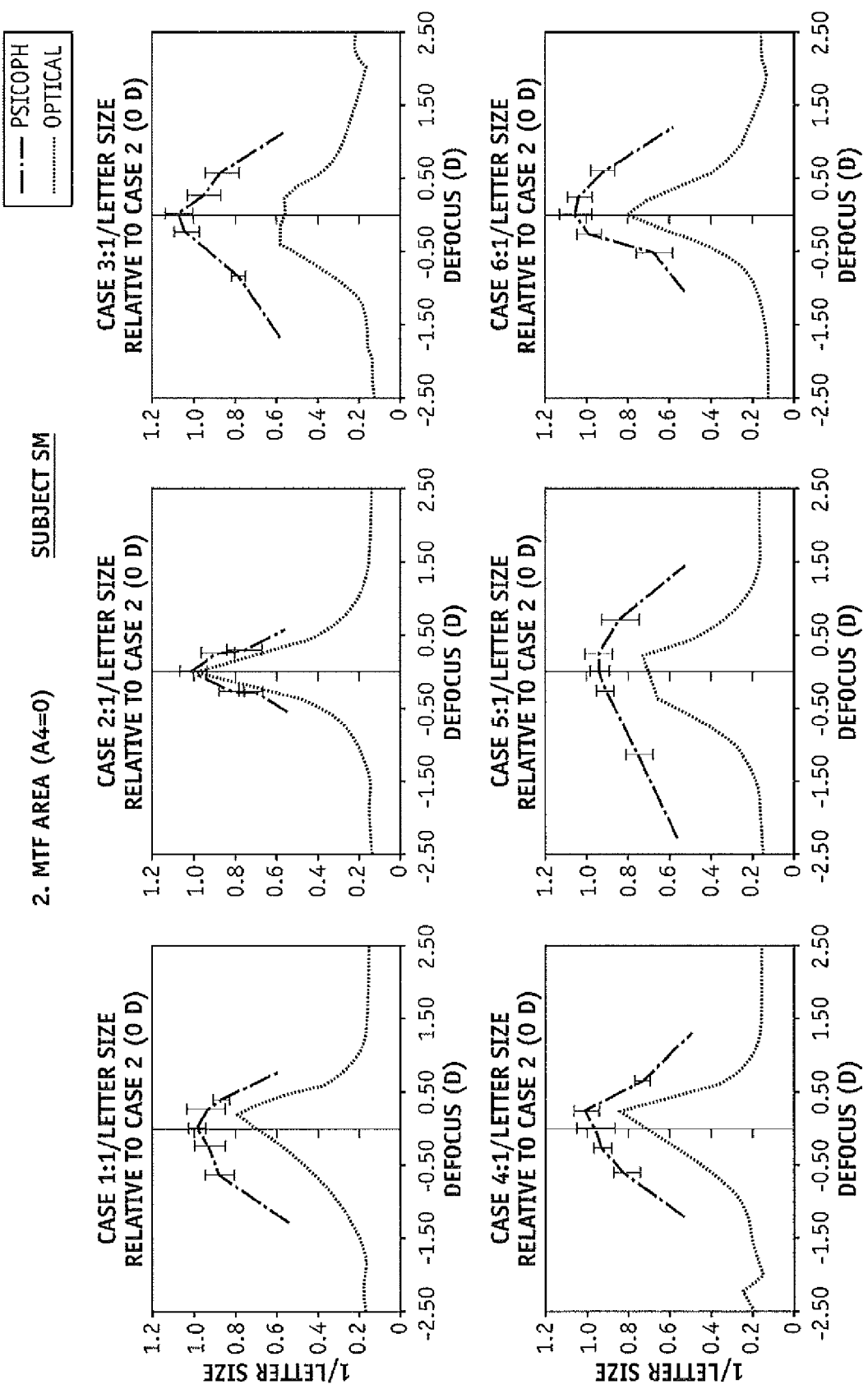
FIG. 16 illustrates comparisons of inverse letter size versus defocus for various aberration correction types of the first subject to Modulation Transfer Function area versus defocus for the respective aberration correction types of the first subject.

FIG. 16 illustrates comparisons of inverse letter size versus defocus for various aberration correction types of the first subject to Modulation Transfer Function area versus defocus for the respective aberration correction types of the first subject. For example, inverse letter size versus defocus for the first aberration correction type of the first subject is compared to Modulation Transfer Function area versus defocus for the first aberration correction type of the first subject, inverse letter size versus defocus for the second aberration correction type of the first subject is compared to Modulation Transfer Function area versus defocus for the second aberration correction type of the first subject, inverse letter size versus defocus for the third aberration correction type of the first subject is compared to Modulation Transfer Function area versus defocus for the third aberration correction type of the first subject, inverse letter size versus defocus for the fourth aberration correction type of the first subject is compared to Modulation Transfer Function area versus defocus for the fourth aberration correction type of the first subject, inverse letter size versus defocus for the fifth aberration correction type of the first subject is compared to Modulation Transfer Function area versus defocus for the fifth aberration correction type of the first subject, and inverse letter size versus defocus for the sixth aberration correction type of the first subject is compared to Modulation Transfer Function area versus defocus for the sixth aberration correction type of the first subject.

Figure 17:
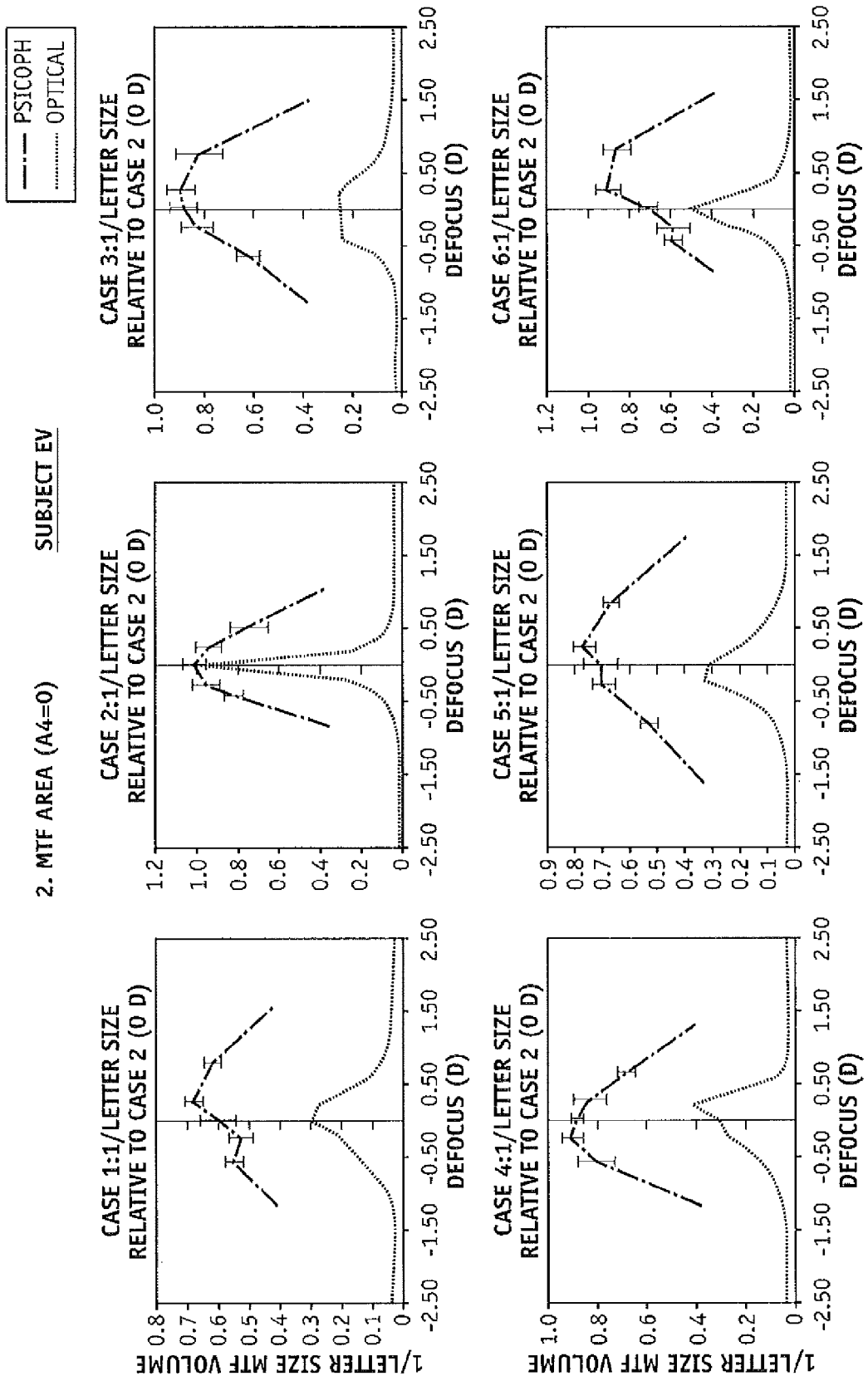
FIG. 17 illustrates comparisons of inverse letter size versus defocus for various aberration correction types of the second subject to Modulation Transfer Function area versus defocus for the respective aberration correction types of the second subject.

FIG. 17 illustrates comparisons of inverse letter size versus defocus for various aberration correction types of the second subject to Modulation Transfer Function area versus defocus for the respective aberration correction types of the second subject. For example, inverse letter size versus defocus for the first aberration correction type of the second subject is compared to Modulation Transfer Function area versus defocus for the first aberration correction type of the second subject, inverse letter size versus defocus for the second aberration correction type of the second subject is compared to Modulation Transfer Function area versus defocus for the second aberration correction type of the second subject, inverse letter size versus defocus for the third aberration correction type of the second subject is compared to Modulation Transfer Function area versus defocus for the third aberration correction type of the second subject, inverse letter size versus defocus for the fourth aberration correction type of the second subject is compared to Modulation Transfer Function area versus defocus for the fourth aberration correction type of the second subject, inverse letter size versus defocus for the fifth aberration correction type of the second subject is compared to Modulation Transfer Function area versus defocus for the fifth aberration correction type of the second subject, and inverse letter size versus defocus for the sixth aberration correction type of the second subject is compared to Modulation Transfer Function area versus defocus for the sixth aberration correction type of the second subject.

Figure 18:
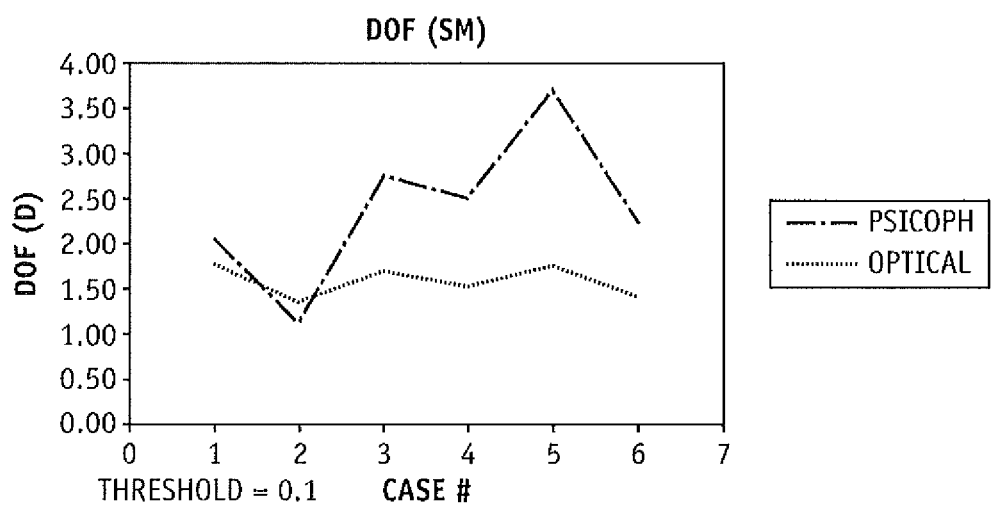
FIG. 18 is a plot of depth of focus versus the aberration correction types shown in FIG. 16 of the first subject and a MTF area threshold of 0.1.
Figure 19:
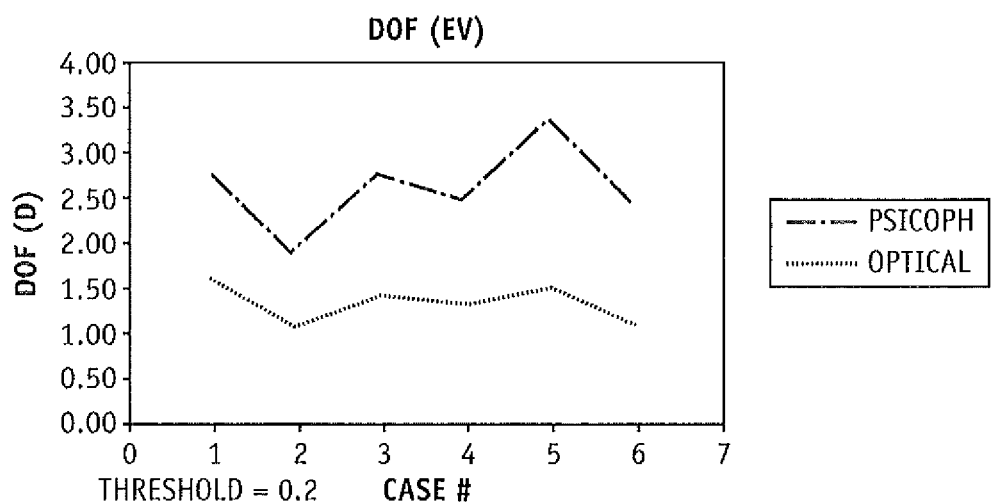
FIG. 19 is a plot of depth of focus versus the aberration correction types shown in FIG. 17 of the second subject and a MTF area threshold of 0.2.

FIG. 18 is a plot of depth of focus versus the aberration correction types shown in FIG. 16 of the first subject and a MTF area threshold of 0.1. FIG. 19 is a plot of depth of focus versus the aberration correction types shown in FIG. 17 of the second subject and a MTF area threshold of 0.2.

Figure 20:
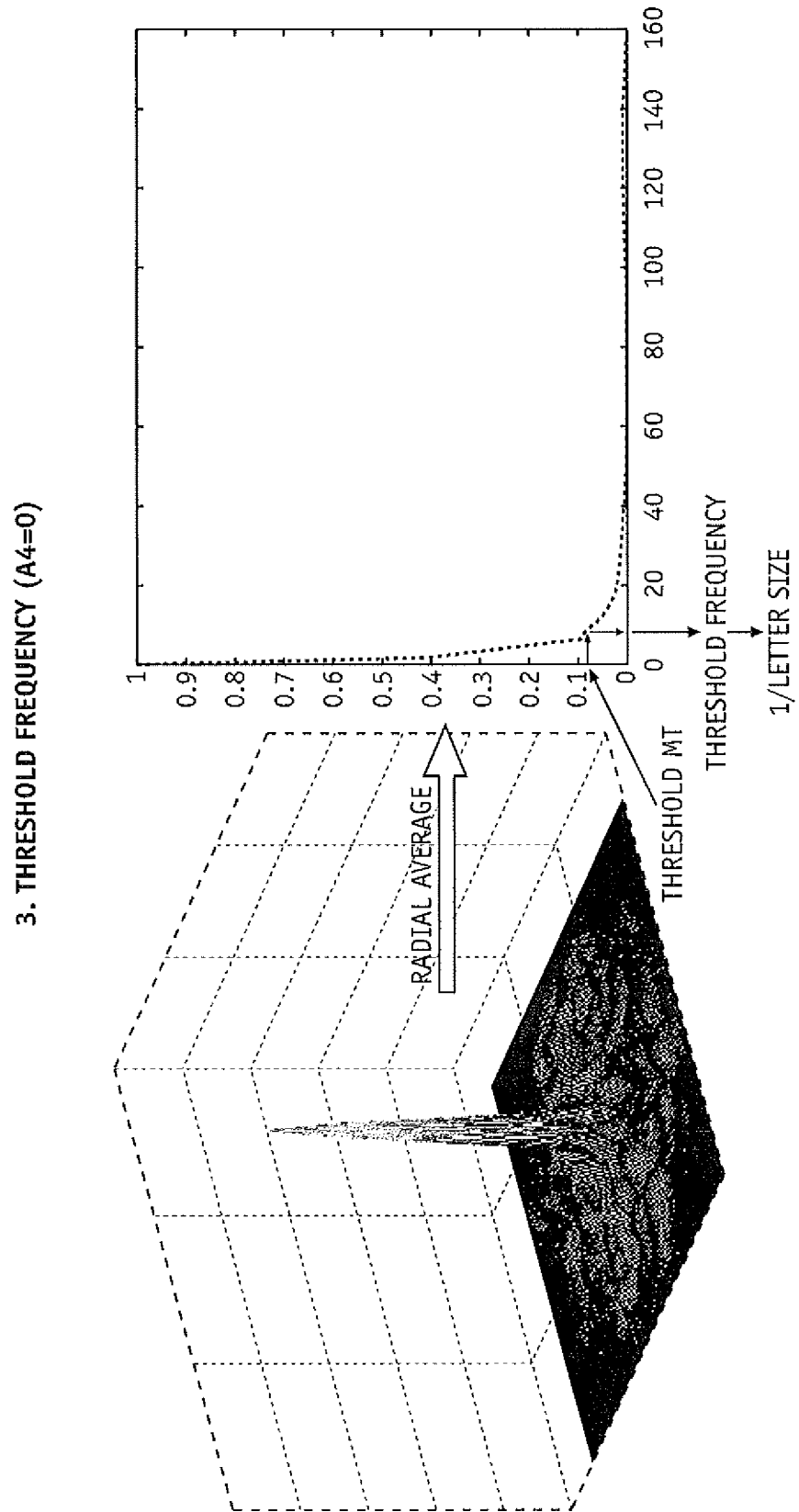
FIG. 20 is a Modulation Transfer Function illustrating a threshold frequency in one embodiment.

FIG. 20 is a Modulation Transfer Function illustrating a threshold frequency in one embodiment. The radial average is used to determine the threshold frequency from a threshold MT.

Figure 21:
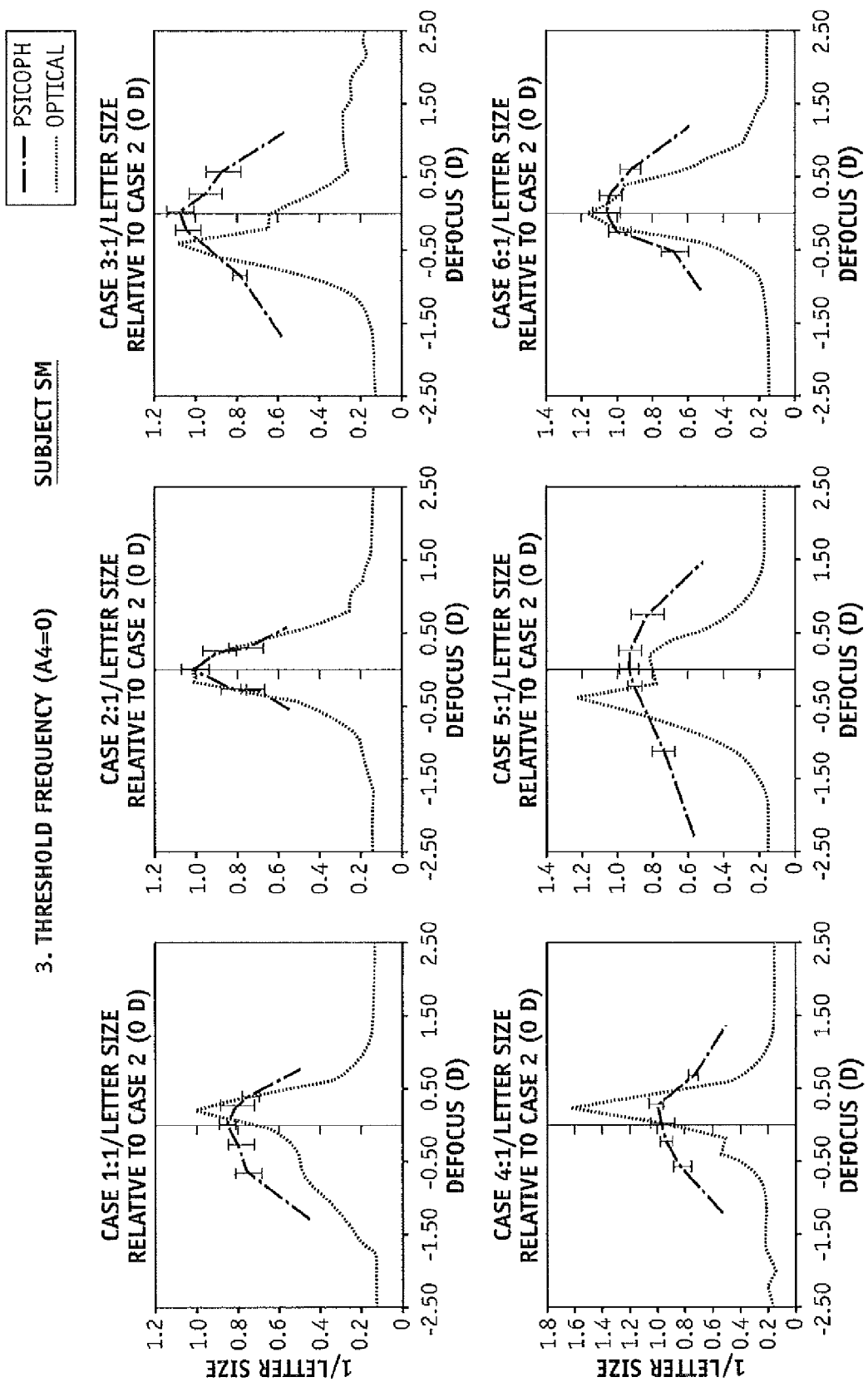
FIG. 21 illustrates comparisons of inverse letter size versus defocus for various aberration correction types of the first subject to threshold frequency versus defocus for the respective aberration correction types of the first subject.

FIG. 21 illustrates comparisons of inverse letter size versus defocus for various aberration correction types of the first subject to threshold frequency versus defocus for the respective aberration correction types of the first subject. For example, inverse letter size versus defocus for the first aberration correction type of the first subject is compared to threshold frequency versus defocus for the first aberration correction type of the first subject, inverse letter size versus defocus for the second aberration correction type of the first subject is compared to threshold frequency versus defocus for the second aberration correction type of the first subject, inverse letter size versus defocus for the third aberration correction type of the first subject is compared to threshold frequency versus defocus for the third aberration correction type of the first subject, inverse letter size versus defocus for the fourth aberration correction type of the first subject is compared to threshold frequency versus defocus for the fourth aberration correction type of the first subject, inverse letter size versus defocus for the fifth aberration correction type of the first subject is compared to threshold frequency versus defocus for the fifth aberration correction type of the first subject, and inverse letter size versus defocus for the sixth aberration correction type of the first subject is compared to threshold frequency versus defocus for the sixth aberration correction type of the first subject.

Figure 22:
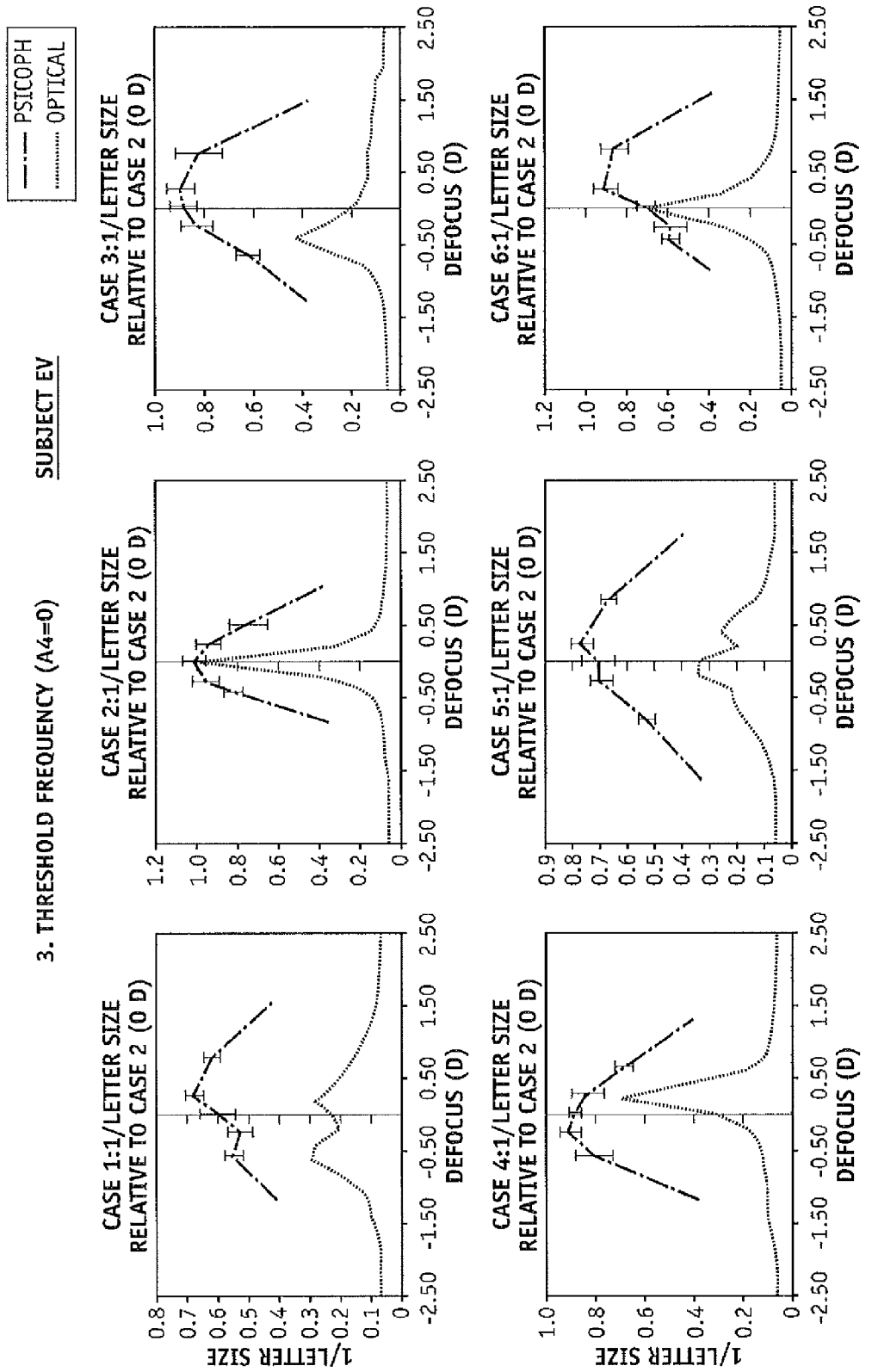
FIG. 22 illustrates comparisons of inverse letter size versus defocus for various aberration correction types of the second subject to threshold frequency versus defocus for the respective aberration correction types of the second subject.

FIG. 22 illustrates comparisons of inverse letter size versus defocus for various aberration correction types of the second subject to threshold frequency versus defocus for the respective aberration correction types of the second subject. For example, inverse letter size versus defocus for the first aberration correction type of the second subject is compared to threshold frequency versus defocus for the first aberration correction type of the second subject, inverse letter size versus defocus for the second aberration correction type of the second subject is compared to threshold frequency versus defocus for the second aberration correction type of the second subject, inverse letter size versus defocus for the third aberration correction type of the second subject is compared to threshold frequency versus defocus for the third aberration correction type of the second subject, inverse letter size versus defocus for the fourth aberration correction type of the second subject is compared to threshold frequency versus defocus for the fourth aberration correction type of the second subject, inverse letter size versus defocus for the fifth aberration correction type of the second subject is compared to threshold frequency versus defocus for the fifth aberration correction type of the second subject, and inverse letter size versus defocus for the sixth aberration correction type of the second subject is compared to threshold frequency versus defocus for the sixth aberration correction type of the second subject.

Figure 23:
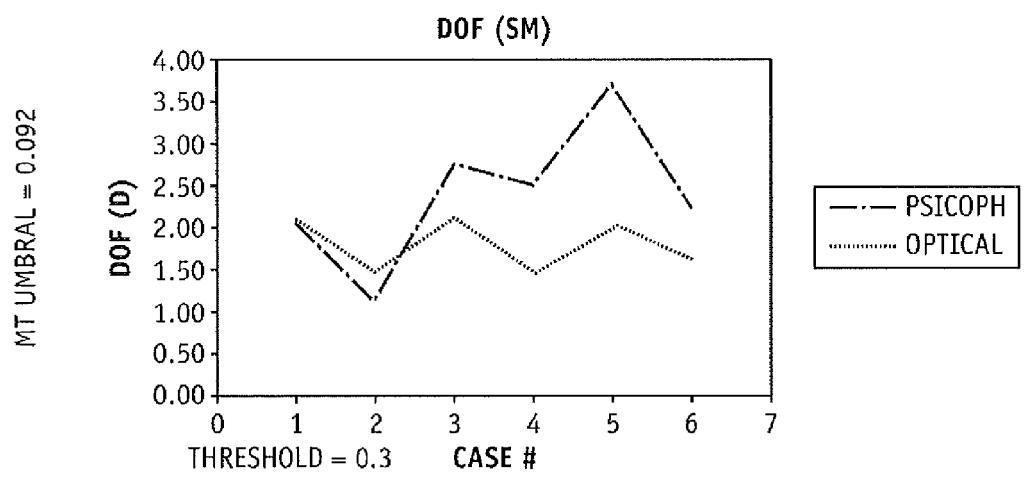
FIG. 23 is a plot of depth of focus versus the aberration correction types determined from the pschophysical measurement and determined from theoretical calculation of the threshold frequency as shown in FIG. 21 of the first subject.
Figure 24:
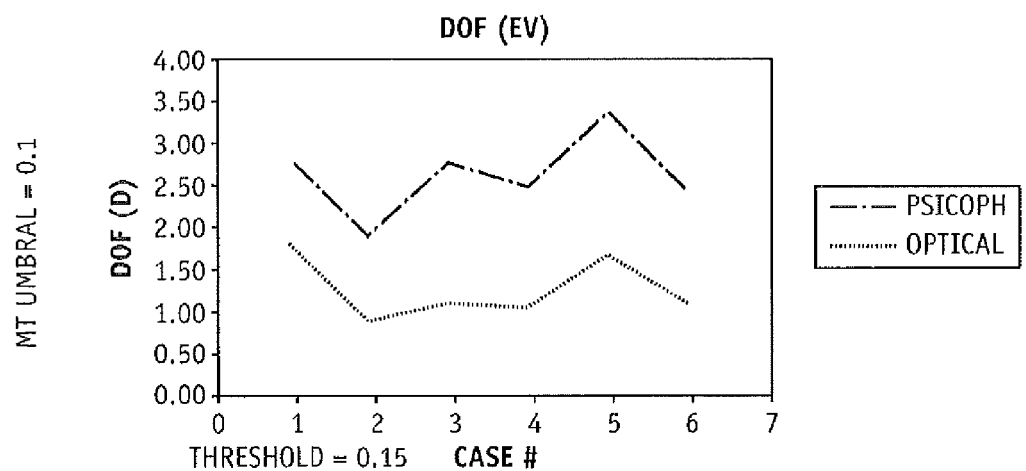
FIG. 24 is a plot of depth of focus versus the aberration correction types determined from the pschophysical measurement and determined from theoretical calculation of the threshold frequency as shown in FIG. 22 of the second subject.

FIG. 23 is a plot of depth of focus versus the aberration correction types determined from the pschophysical measurement and determined from theoretical calculation of the threshold frequency as shown in FIG. 21 of the first subject. FIG. 24 is a plot of depth of focus versus the aberration correction types determined from the pschophysical measurement and determined from theoretical calculation of the threshold frequency as shown in FIG. 22 of the second subject.

Figure 25:
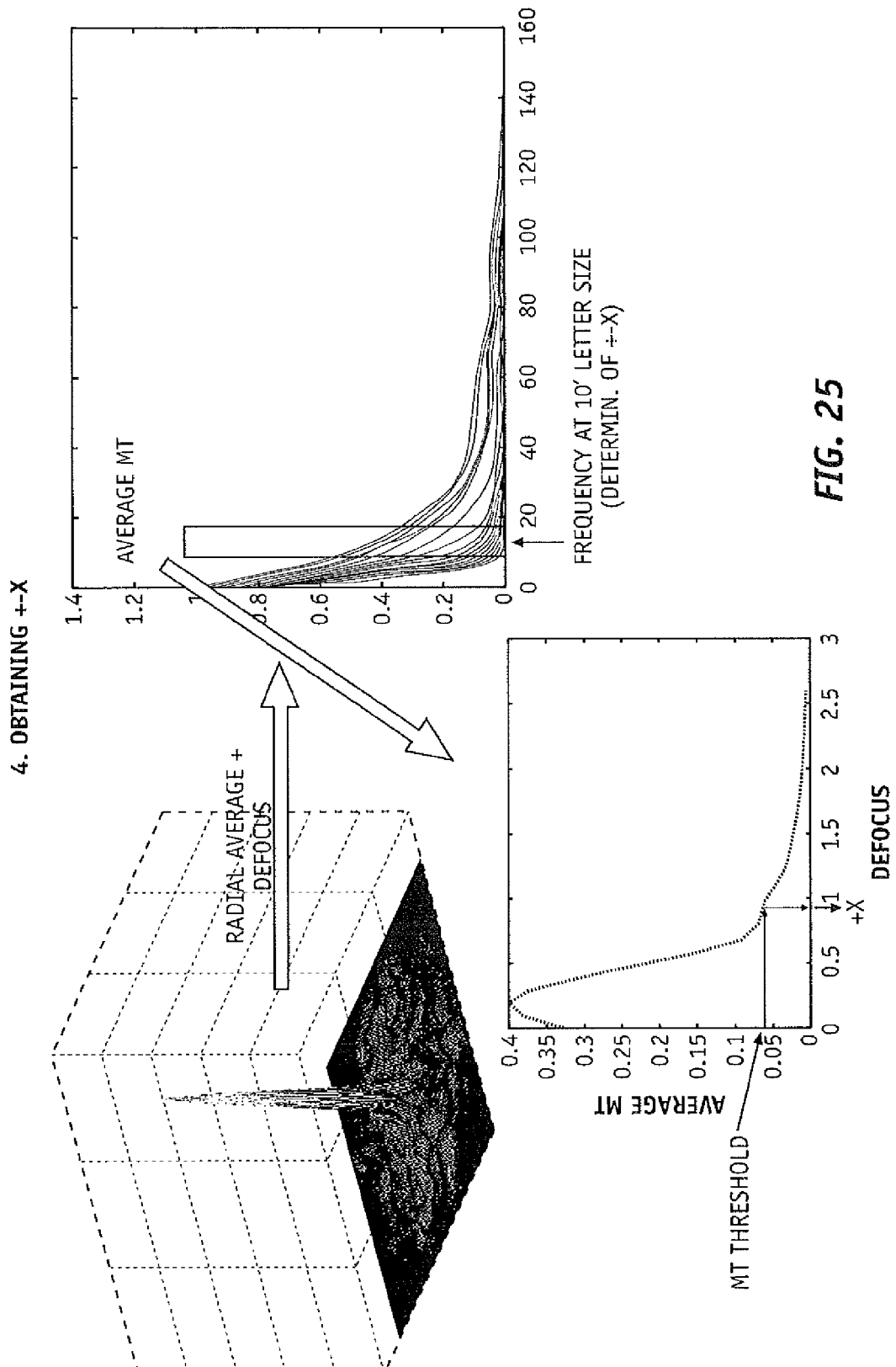
FIG. 25 is a Modulation Transfer Function illustrating a method for determining a Modulation Transfer threshold that is determined from MT values calculated for the 10' letter size (termed ±x) in one embodiment.

FIG. 25 is a Modulation Transfer Function illustrating a method for determining a Modulation Transfer threshold that is determined from MT values calculated for the 10' letter size (termed ±x) in one embodiment.

Figure 26:
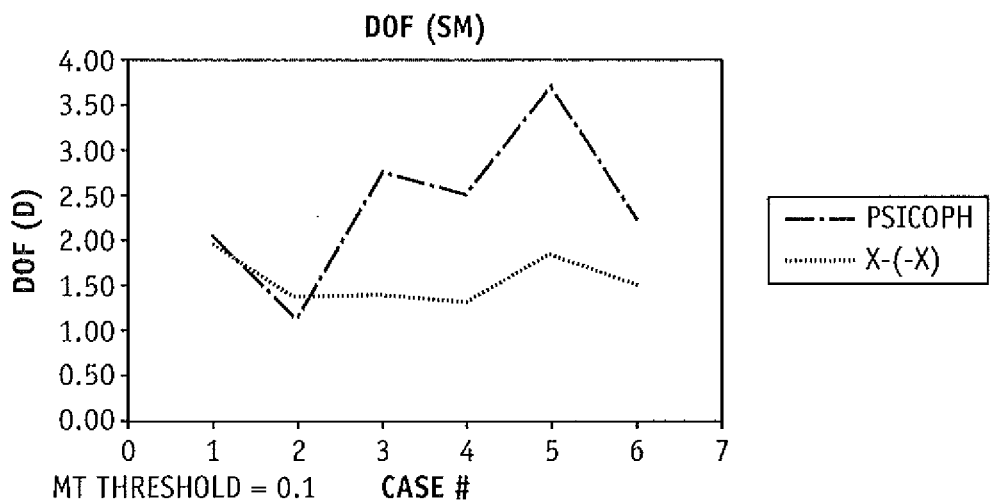
FIG. 26 is a plot of depth of focus versus the aberration correction types determined from the pschophysical measurement and determined from theoretical calculation of ±x of the first subject.
Figure 27:
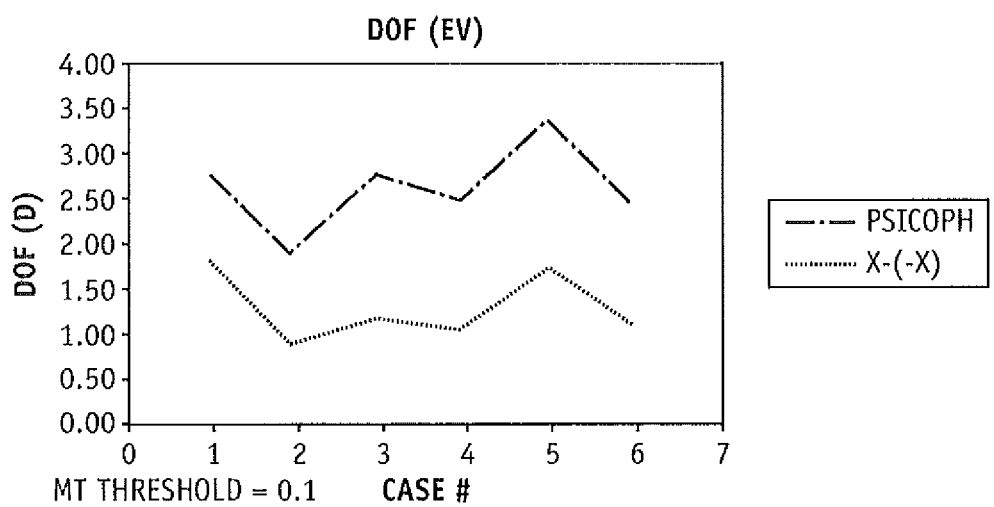
FIG. 27 is a plot of depth of focus versus the aberration correction types shown determined from the pschophysical measurement and determined from theoretical calculation of ±x of the second subject.

FIG. 26 is a plot of depth of focus versus the aberration correction types determined from the pschophysical measurement and determined from theoretical calculation of ±x of the first subject. FIG. 27 is a plot of depth of focus versus the aberration correction types shown determined from the pschophysical measurement and determined from theoretical calculation of ±x of the second subject.

Figure 28:
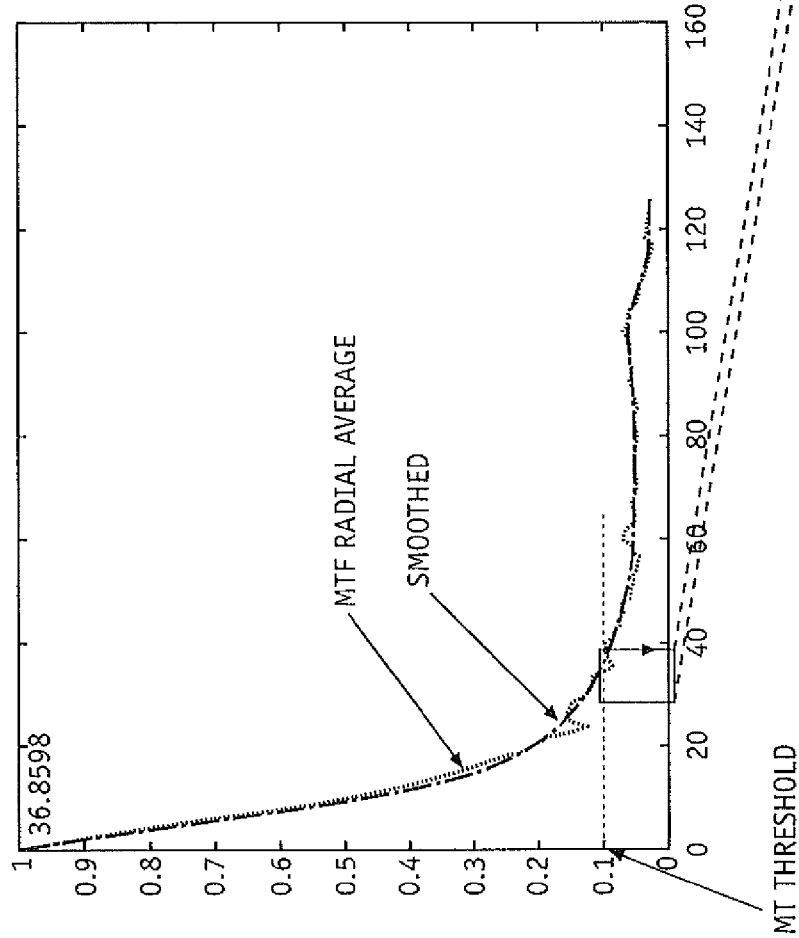
FIG. 28 is a Modulation Transfer Function illustrating an MTF volume within a frequency range in one embodiment.
Figure 28:
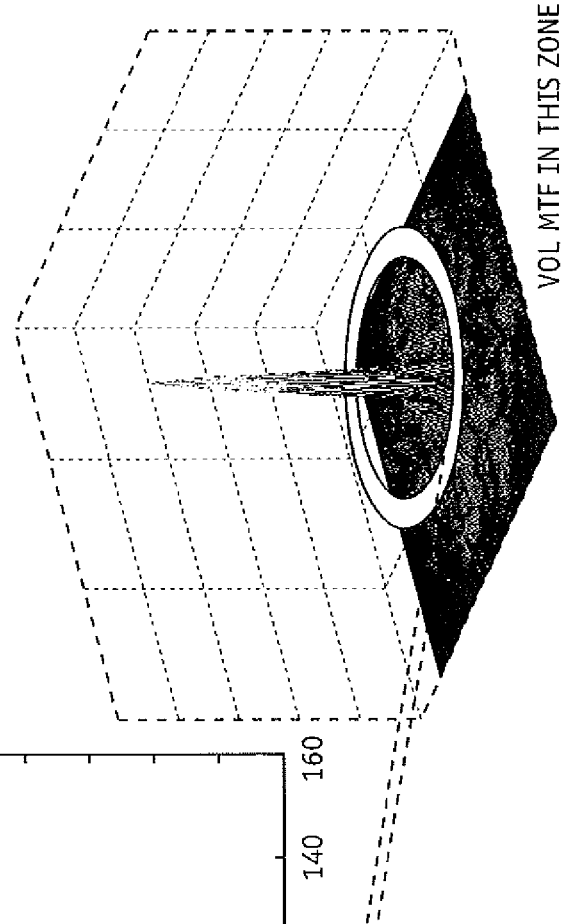

FIG. 28 is a Modulation Transfer Function illustrating an MTF volume within a frequency range in one embodiment.

Figure 29:
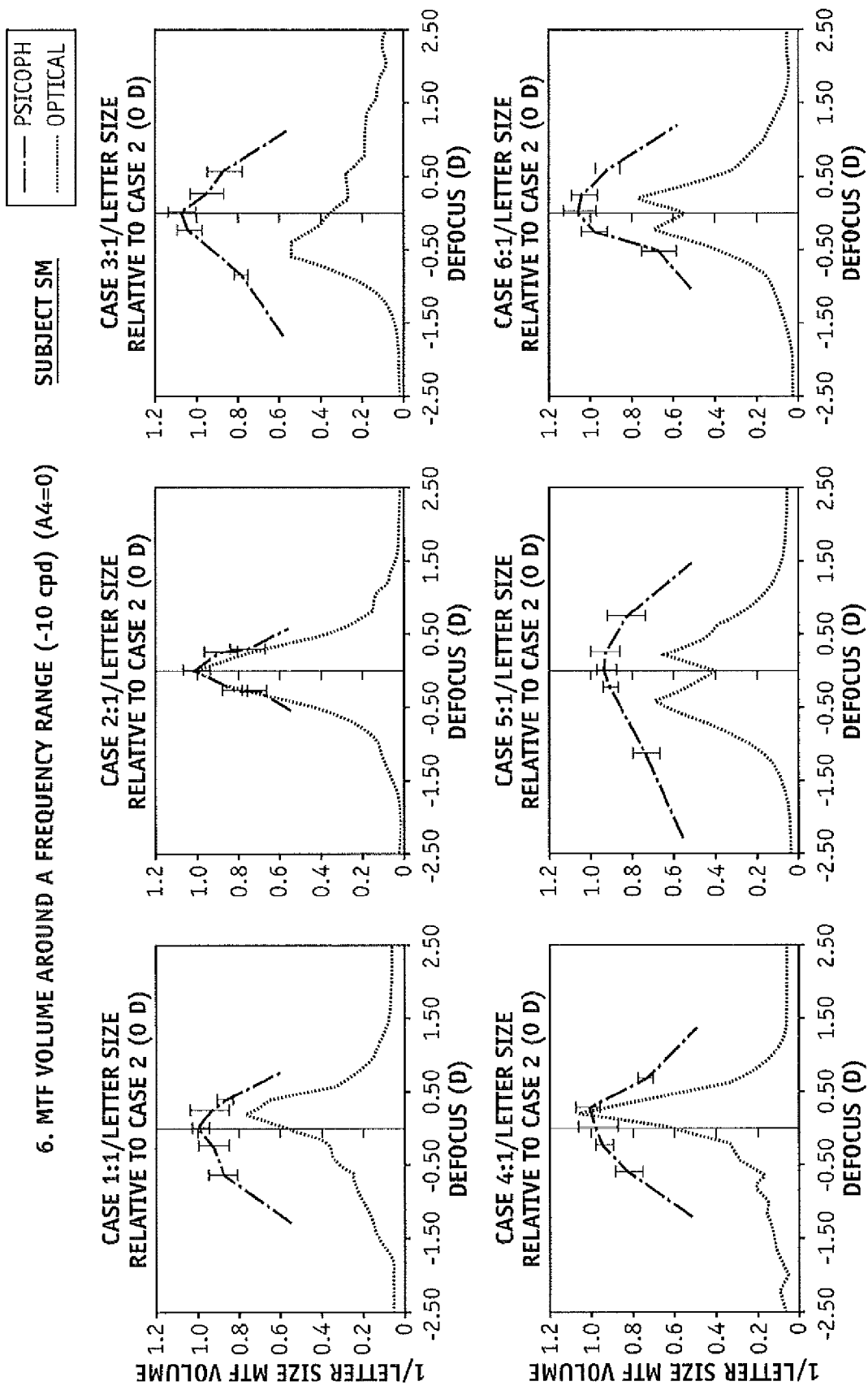
FIG. 29 illustrates comparisons of inverse letter size versus defocus for various aberration correction types of the first subject to MTF volume within a frequency range versus defocus for the respective aberration correction types of the first subject.

FIG. 29 illustrates comparisons of inverse letter size versus defocus for various aberration correction types of the first subject to MTF volume within a frequency range versus defocus for the respective aberration correction types of the first subject. For example, inverse letter size versus defocus for the first aberration correction type of the first subject is compared to MTF volume within a frequency range versus defocus for the first aberration correction type of the first subject, inverse letter size versus defocus for the second aberration correction type of the first subject is compared to MTF volume within a frequency range versus defocus for the second aberration correction type of the first subject, inverse letter size versus defocus for the third aberration correction type of the first subject is compared to MTF volume within a frequency range versus defocus for the third aberration correction type of the first subject, inverse letter size versus defocus for the fourth aberration correction type of the first subject is compared to MTF volume within a frequency range versus defocus for the fourth aberration correction type of the first subject, inverse letter size versus defocus for the fifth aberration correction type of the first subject is compared to MTF volume within a frequency range versus defocus for the fifth aberration correction type of the first subject, and inverse letter size versus defocus for the sixth aberration correction type of the first subject is compared to MTF volume within a frequency range versus defocus for the sixth aberration correction type of the first subject.

Figure 30:
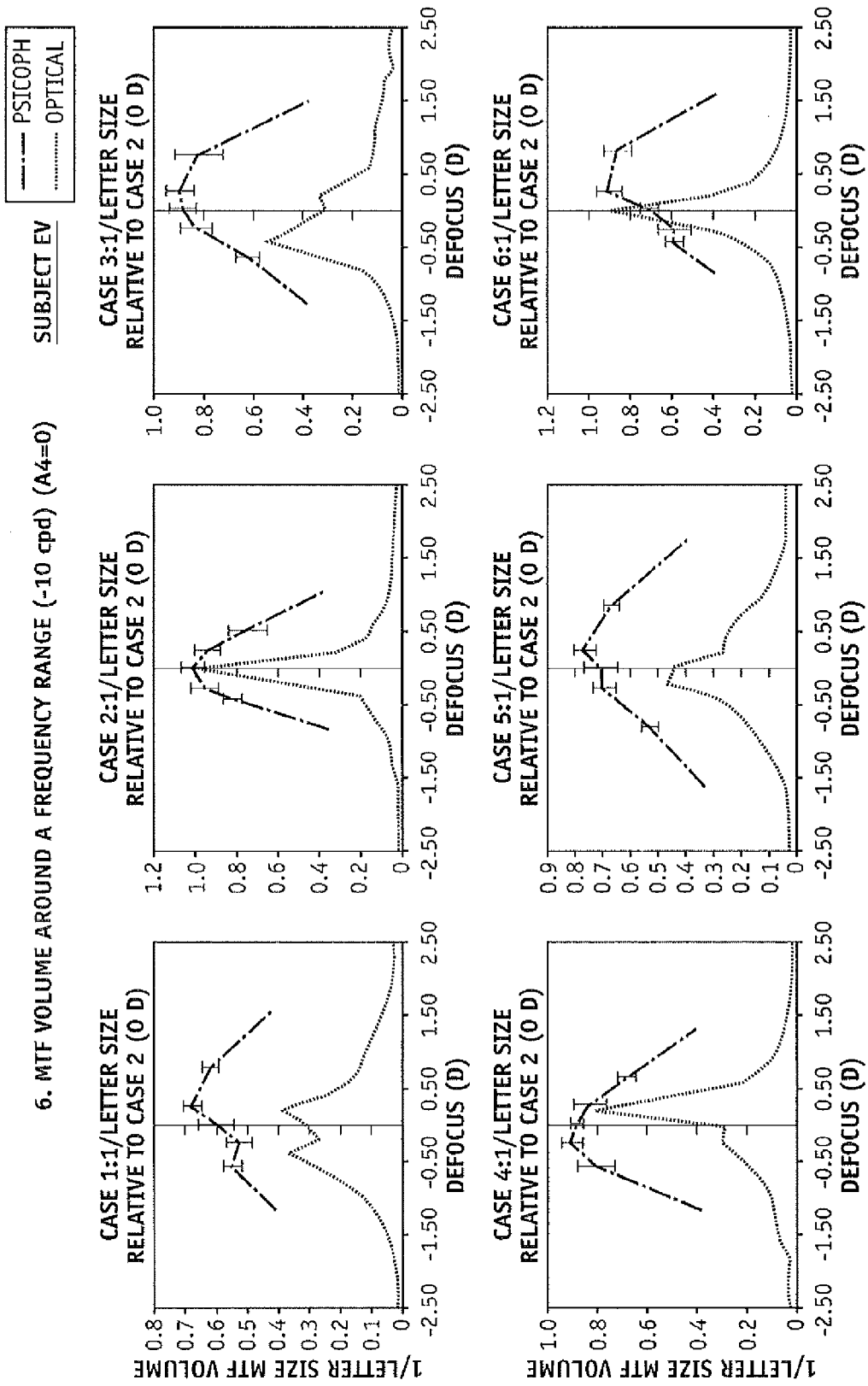
FIG. 30 illustrates comparisons of inverse letter size versus defocus for various aberration correction types of the second subject to MTF volume within a frequency range versus defocus for the respective aberration correction types of the second subject.

FIG. 30 illustrates comparisons of inverse letter size versus defocus for various aberration correction types of the second subject to MTF volume within a frequency range versus defocus for the respective aberration correction types of the second subject. For example, inverse letter size versus defocus for the first aberration correction type of the second subject is compared to MTF volume within a frequency range versus defocus for the first aberration correction type of the second subject, inverse letter size versus defocus for the second aberration correction type of the second subject is compared to MTF volume within a frequency range versus defocus for the second aberration correction type of the second subject, inverse letter size versus defocus for the third aberration correction type of the second subject is compared to MTF volume within a frequency range versus defocus for the third aberration correction type of the second subject, inverse letter size versus defocus for the fourth aberration correction type of the second subject is compared to MTF volume within a frequency range versus defocus for the fourth aberration correction type of the second subject, inverse letter size versus defocus for the fifth aberration correction type of the second subject is compared to MTF volume within a frequency range versus defocus for the fifth aberration correction type of the second subject, and inverse letter size versus defocus for the sixth aberration correction type of the second subject is compared to MTF volume within a frequency range versus defocus for the sixth aberration correction type of the second subject.

Figure 31:
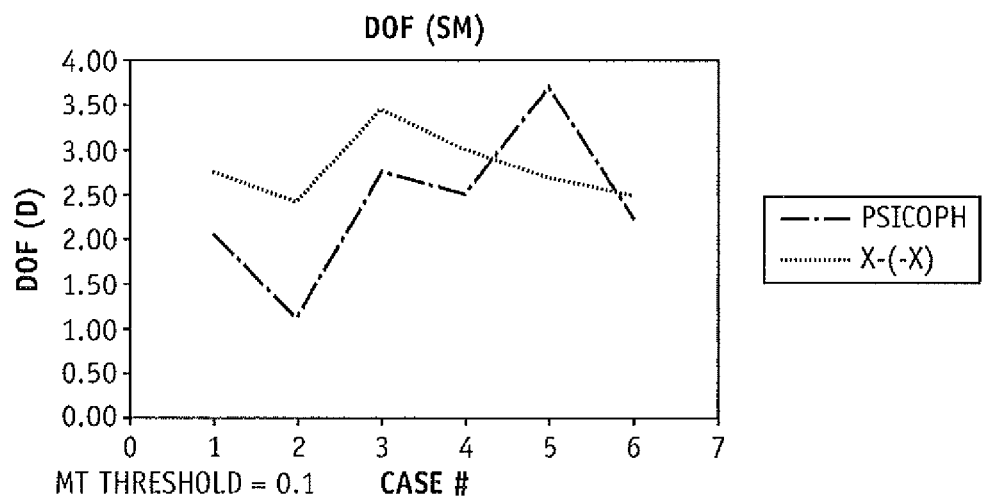
FIG. 31 is a plot of depth of focus versus the aberration correction types determined from the pschophysical measurement and determined from theoretical calculation of MTF volume within a frequency range shown in FIG. 29 of the first subject.
Figure 32:
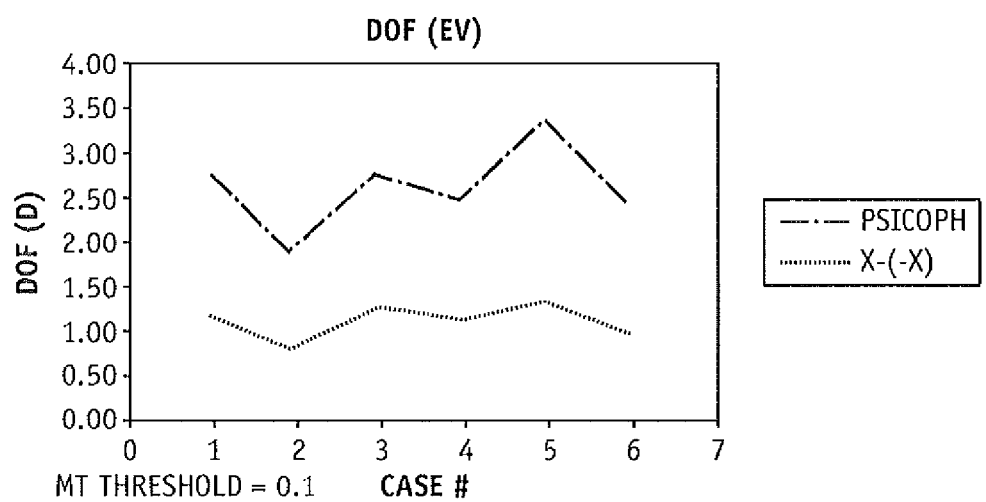
FIG. 32 is a plot of depth of focus versus the aberration correction types determined from the pschophysical measurement and determined from theoretical calculation of MTF volume within a frequency range shown in FIG. 30 of the second subject.

FIG. 31 is a plot of depth of focus versus the aberration correction types determined from the pschophysical measurement and determined from theoretical calculation of MTF volume within a frequency range shown in FIG. 29 of the first subject. FIG. 32 is a plot of depth of focus versus the aberration correction types determined from the pschophysical measurement and determined from theoretical calculation of MTF volume within a frequency range shown in FIG. 30 of the second subject.

Figure 33:
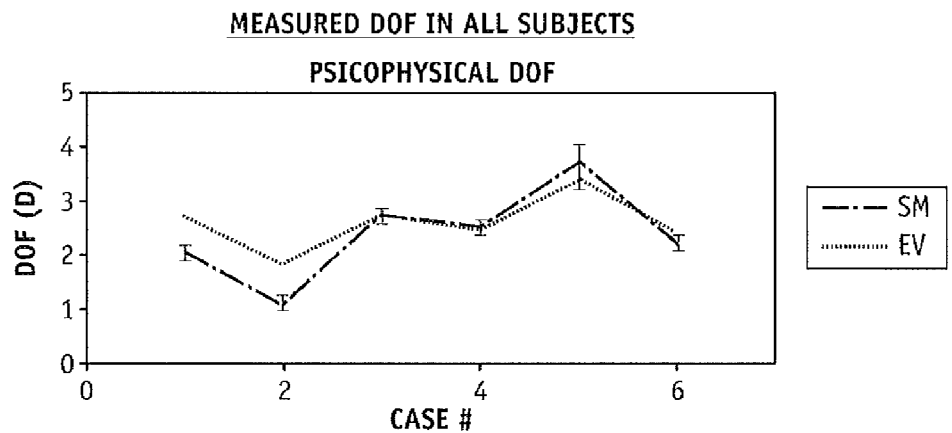
FIG. 33 is a plot of measured depth of focus versus the aberration correction types for the first and second subjects.

FIG. 33 is a plot of measured depth of focus versus the aberration correction types for the first and second subjects.

Figure 34:
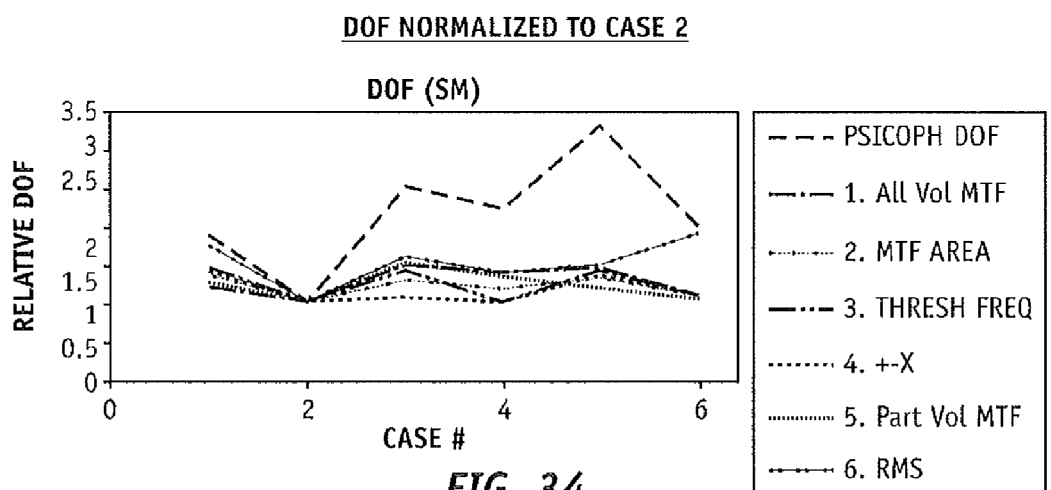
FIG. 34 is a plot comparing depth of focus measured pschophysically to depth of focus calculated with all theoretical methods versus the aberration correction types for the first subject.
Figure 35:
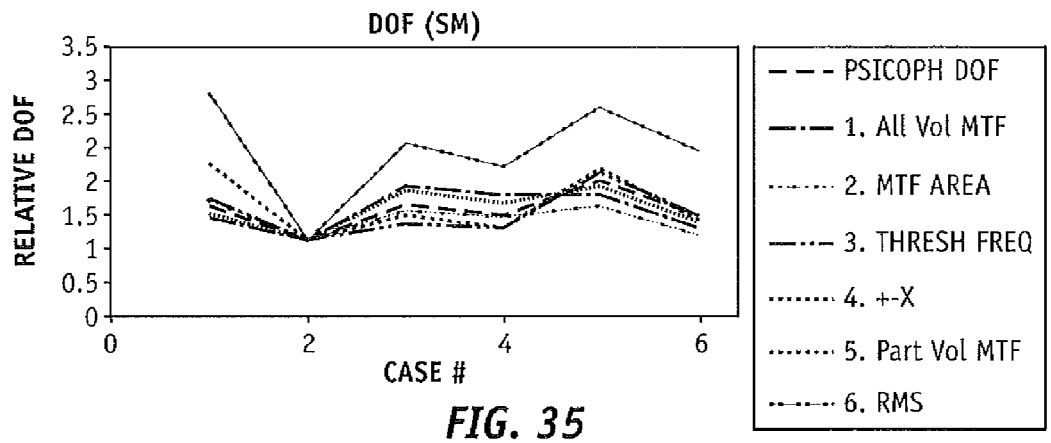
FIG. 35 is a plot comparing depth of focus measured pschophysically to depth of focus calculated with all theoretical methods versus the aberration correction types for the second subject.

FIG. 34 is a plot comparing depth of focus measured pschophysically to depth of focus calculated with all theoretical methods versus the aberration correction types for the first subject. FIG. 35 is a plot comparing depth of focus measured pschophysically to depth of focus calculated with all theoretical methods versus the aberration correction types for the second subject.

In some embodiments, other ophthalmic devices and designs may additionally be incorporated to extend the depth of focus of monofocal, multifocal, or even accommodating intraocular lenses. Such ophthalmic devices and designs include, but are not limited to, those disclosed in U.S. Pat. No. 6,126,286 (Portney) and U.S. Pat. No. 6,923,539 (Simpson et al.), and U.S. Patent Application Number 20060116763A1 (Simpson), all of which are herein incorporated by reference in their entirety. In certain embodiments, the surface profile may initially have something similar to those taught in U.S. Pat. Nos. 6,126,286 or 6,923,539, or U.S. Pub. No. 20060116763A1. This may be used in combination with the introduction of asymmetric aberration to provide both an extended depth of focus and a predetermined visual acuity performance.

In some embodiments, an extended or expanded depth of focus is provided by an ophthalmic lens or optic comprising a phase-affecting, non-diffractive mask to increase the depth of focus of an ophthalmic lens. In such embodiments, the ophthalmic lens may include one or more spatially low frequency phase transitions, for example, as disclosed in U.S. Pat. No. 7,061,693, which is herein incorporated by reference in its entirety. Such a non-diffractive mask may be used in combination with at least one of the surfaces 2, 3, either on the same or an opposite surface to provide an optic that provides an extended depth of focus with a predetermined optical performance or visual acuity characteristic.

Analysis and storage of the wavefront characteristics of the eye as well as the evaluation, determination, and implementation of asymmetric aberration inducement (i.e., for extending the depth of focus) may be maintained by a control system including computer hardware and/or software, often including one or more programmable processing units operable to execute machine readable program instructions or code for implementing some or all of one or more of the methods described herein. The code is often embodied in a tangible media such as a memory (optionally a read only memory, a random access memory, a non-volatile memory, or the like) and/or a recording media (such as a floppy disk, a hard drive, a CD, a DVD, a memory stick, or the like). The code and/or associated data and signals may also be transmitted to or from the control system via a network connection (such as a wireless network, an Ethernet, an internet, an intranet, or the like) to the system, and some or all of the code may also be transmitted between components of the system and/or within the system via one or more bus, and appropriate standard or proprietary communications cards, connectors, cables, and the like will often be included in the system. The system is often configured to perform the calculations and signal transmission steps described herein at least in part by programming with the software code, which may be written as a single program, a series of separate subroutines or related programs, or the like. Standard or proprietary digital and/or analog signal processing hardware, software, and/or firmware may be utilized, and will typically have sufficient processing power to perform the calculations described herein during treatment of the patient. The system optionally includes a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with computer systems may also be included, and processors having a plurality of processing units (or even separate computers) may be employed in a wide range of centralized or distributed data processing architectures.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention. The invention, therefore, is not to be restricted except in the spirit of the following claims.

What is claimed is:

1. A method for modifying a depth of focus of an eye, the method comprising the steps of:
   measuring a wavefront aberration of the eye;
   determining an in-focus visual acuity of the eye; and
   determining a asymmetric aberration to be induced in the wavefront aberration of the eye, the depth of focus being extended by the asymmetric aberration when induced in the wavefront aberration and while maintaining the in-focus visual acuity;
   forming a multifocal ophthalmic lens, having at least two focal points, one to correct near vision and one to correct far vision, and configured to introduce the asymmetric aberration;
   wherein the forming step comprises one of a group consisting of:
   lathe-cutting an ophthalmic lens having first and second opposing surfaces, the first and second opposing surfaces together configured to introduce the asymmetric aberration to the eye; and
      molding an ophthalmic lens having first and second opposing surfaces, the first and second opposing surfaces together configured to introduce the asymmetric aberration to the eye,
   wherein the introduced asymmetric aberration extends the depth of focus associated with each of the at least two focal points.

2. The method of claim 1, further comprising inducing the asymmetric aberration in the wavefront aberration.

3. The method of claim 2, wherein the step of inducing is selected from a group consisting of:
   implanting an intraocular lens configured to introduce the asymmetric aberration to the eye while maintaining the in-focus visual acuity;
   positioning an ophthalmic lens adjacent the eye, the ophthalmic lens configured to introduce the asymmetric aberration to the eye while maintaining the in-focus visual acuity;
   photoaltering a cornea of the eye to introduce the asymmetric aberration to the eye while maintaining the in-focus visual acuity;
   implanting a corneal tissue portion in the cornea of the eye, the corneal tissue configured to introduce the asymmetric aberration to the eye while maintaining the in-focus visual acuity; and
   inserting an intracorneal implant in the cornea of the eye, the intracorneal implant configured to introduce the asymmetric aberration to the eye while maintaining the in-focus visual acuity.

4. The method of claim 1, wherein the step of determining an asymmetric aberration comprises:
   selecting an asymmetric aberration type from a group consisting of an asymmetric astigmatism, a higher order astigmatism, a vertical coma, a lateral coma, and a trefoil; and
   determining an amount of the asymmetric aberration type to extend the depth of focus while maintaining the in-focus visual acuity.

\* \* \* \* \*